(12) United States Patent
Fuller et al.

(10) Patent No.: US 11,081,274 B2
(45) Date of Patent: Aug. 3, 2021

(54) WIRELESSLY POWERED DEVICES FOR MINIMALLY INVASIVE SURGERY

(71) Applicant: Greatbatch Ltd., Clarence, NY (US)

(72) Inventors: Michael J. Fuller, Worcester, MA (US); Brian R. Peterson, Cumberland, RI (US); Jason Hamilton, Dartmouth, MA (US); Leslie I. Halberg, Valencia, CA (US); Eric Jankins, Raynham, MA (US); Gregory G. Decker, Terrace, MA (US)

(73) Assignee: Greatbatch Ltd., Clarence, NY (US)

( * ) Notice: Subject to any disclaimer, the term of this patent is extended or adjusted under 35 U.S.C. 154(b) by 619 days.

(21) Appl. No.: 15/902,242

(22) Filed: Feb. 22, 2018

(65) Prior Publication Data
US 2018/0247759 A1    Aug. 30, 2018

Related U.S. Application Data

(60) Provisional application No. 62/463,334, filed on Feb. 24, 2017, provisional application No. 62/557,329, filed on Sep. 12, 2017.

(51) Int. Cl.
*H01F 38/14* (2006.01)
*A61B 1/06* (2006.01)
(Continued)

(52) U.S. Cl.
CPC ......... *H01F 38/14* (2013.01); *A61B 1/00009* (2013.01); *A61B 1/06* (2013.01);
(Continued)

(58) Field of Classification Search
CPC ........ H02J 50/001; H02J 50/005; H02J 50/10; H02J 50/12; H02J 50/30; H02J 50/40;
(Continued)

(56) References Cited

U.S. PATENT DOCUMENTS

| 5,849,020 A | 12/1998 | Freeman et al. |
| 9,755,456 B1 | 9/2017 | Jankins et al. |

(Continued)

FOREIGN PATENT DOCUMENTS

| EP | 2067501 | 6/2009 |
| JP | 2000254134 | 9/2000 |

(Continued)

OTHER PUBLICATIONS

Goel, S, Suweg, BS, Ranjan, P. Remote interface for slider aided wireless power transmission. Amity University Uttar Pradesh, May 19, 2015 (Year: 2015).*

(Continued)

*Primary Examiner* — Jennifer Pitrak McDonald
*Assistant Examiner* — Shreya Anjaria
(74) *Attorney, Agent, or Firm* — Michael P. Horvath

(57) ABSTRACT

In various examples, a system for wirelessly transmitting power using resonant magnetic field power transfer includes a device including at least one component to be wirelessly powered. The device includes an elongate shaft and a capture element including a capture coil. A source element for wirelessly supplying power to the device includes a source coil disposed around an opening. The opening is sized to allow the elongate shaft of the device to fit therein. The source is located proximate a surgical access point, wherein, with insertion of the elongate shaft within the opening of the source for surgical access, the capture coil is disposed sufficiently proximate the source coil to allow power to be wirelessly transmitted from the source coil to the capture coil to power the at least one component of the device.

20 Claims, 14 Drawing Sheets

(51) Int. Cl.
| | |
|---|---|
| *A61B 1/00* | (2006.01) |
| *A61B 18/14* | (2006.01) |
| *A61M 29/02* | (2006.01) |
| *A61C 3/02* | (2006.01) |
| *A61C 1/06* | (2006.01) |
| *H02J 50/12* | (2016.01) |
| *A61B 17/00* | (2006.01) |
| *A61B 17/16* | (2006.01) |
| *A61B 17/34* | (2006.01) |
| *A61B 18/08* | (2006.01) |
| *A61B 17/32* | (2006.01) |
| *A61B 17/068* | (2006.01) |
| *A61B 18/00* | (2006.01) |
| *A61B 17/29* | (2006.01) |
| *A61B 17/072* | (2006.01) |
| *A61B 90/00* | (2016.01) |

(52) U.S. Cl.
CPC ........ *A61B 17/00234* (2013.01); *A61B 17/16* (2013.01); *A61B 17/1628* (2013.01); *A61B 17/3421* (2013.01); *A61B 18/085* (2013.01); *A61B 18/14* (2013.01); *A61C 1/06* (2013.01); *A61C 3/02* (2013.01); *A61M 29/02* (2013.01); *H02J 50/12* (2016.02); *A61B 1/00004* (2013.01); *A61B 17/068* (2013.01); *A61B 17/072* (2013.01); *A61B 17/1626* (2013.01); *A61B 17/29* (2013.01); *A61B 17/320092* (2013.01); *A61B 2017/00017* (2013.01); *A61B 2017/00084* (2013.01); *A61B 2017/00221* (2013.01); *A61B 2017/00398* (2013.01); *A61B 2017/00411* (2013.01); *A61B 2017/2912* (2013.01); *A61B 2017/320094* (2017.08); *A61B 2017/320095* (2017.08); *A61B 2018/00595* (2013.01); *A61B 2018/00601* (2013.01); *A61B 2090/061* (2016.02); *A61B 2090/064* (2016.02); *A61B 2217/005* (2013.01); *A61B 2217/007* (2013.01)

(58) Field of Classification Search
CPC ........ H02J 50/402; H02J 50/50; H02J 50/502; H02J 50/60; H02J 50/70; H02J 50/80; H02J 50/90; H02J 7/00; H02J 7/0042; H02J 7/0044; H02J 7/0045; A61B 18/14; A61B 17/00234; A61B 17/16; A61B 17/3421; A61B 17/1628; A61B 17/072; A61B 17/1626; A61B 17/29; A61B 17/320092; A61B 17/068; A61B 18/085; A61B 2217/007; A61B 2217/005; A61B 1/06; A61B 1/00009; A61B 1/0004; A61B 2090/061; A61B 2090/064; A61B 2017/2912; A61B 2017/00017; A61B 2017/00411; A61B 2017/00084; A61B 2017/00221; A61B 2017/00398; A61B 2017/320095; A61B 2017/320094; H01F 38/14; A61M 29/02; A61C 3/02; A61C 1/06

See application file for complete search history.

(56) References Cited

U.S. PATENT DOCUMENTS

| | | |
|---|---|---|
| 9,842,686 B2 | 12/2017 | Jankins et al. |
| 2008/0113621 A1 | 5/2008 | Parthasarathy et al. |
| 2010/0052431 A1 | 3/2010 | Mita et al. |
| 2010/0294829 A1 | 11/2010 | Giordano et al. |
| 2011/0132963 A1 | 6/2011 | Giordano et al. |
| 2011/0218402 A1 | 9/2011 | Sato et al. |
| 2012/0200685 A1 | 8/2012 | Kawasaki et al. |
| 2013/0009462 A1 | 1/2013 | Amano et al. |
| 2014/0066954 A1 | 3/2014 | Fowler et al. |
| 2015/0057653 A1* | 2/2015 | Sugiyama ........ H01B 3/30 606/34 |
| 2015/0130407 A1 | 5/2015 | Ni et al. |
| 2015/0222127 A1 | 8/2015 | Hansen |
| 2016/0187519 A1* | 6/2016 | Widmer ........ B60L 53/12 324/222 |
| 2016/0254694 A1 | 9/2016 | Peterson et al. |
| 2016/0291095 A1* | 10/2016 | Bell ........ B60L 53/126 |
| 2017/0035402 A1* | 2/2017 | Matsui ........ H02J 50/12 |
| 2017/0296178 A1* | 10/2017 | Miller ........ A61B 5/0261 |

FOREIGN PATENT DOCUMENTS

| | | |
|---|---|---|
| WO | 2006044550 | 4/2006 |
| WO | 2015198618 | 12/2015 |
| WO | 2016135951 | 9/2016 |
| WO | 2016157504 | 10/2016 |
| WO | 2016157525 | 10/2016 |

OTHER PUBLICATIONS

Batteries Not Included: A Mat-Based Wireless Power Transfer System for Implantable Medical Devices As a Moving Target, Article in IEEE Microwave Magazine—Mar. 2013, Qi Xu et al., pp. 63-72.

* cited by examiner

WIRELESSLY POWERED DEVICES FOR MINIMALLY INVASIVE SURGERY

CROSS REFERENCE TO RELATED APPLICATIONS

This application claims the benefit of priority to U.S. Provisional Application Ser. No. 62/463,334, filed on Feb. 24, 2017, entitled "WIRELESS POWER TRANSMISSION SOURCE, CAPTURE AND REPEATER FOR MINIMALLY INVASIVE SURGICAL INSTRUMENTS," and U.S. Provisional Application Ser. No. 62/557,329, filed on Sep. 12, 2017, entitled "WIRELESS POWERED DEVICES FOR MINIMALLY INVASIVE SURGERY," each of which is each incorporated by reference herein in its entirety.

BACKGROUND

The present invention relates to wirelessly powering a device, and more specifically relates to wirelessly transmitting power to a device for minimally invasive surgery.

Many surgical instruments require power to function and currently use cables to communicate power and information between the instrument and a console. Such cables cause ergonomic problems with the balance and ease of use of instruments, as well as a potential safety hazard with many wires underfoot. These wires and cables are not static, as they are attached to devices whose use is mobile, making the cable landscape in the operating room ever changing and difficult to predict over the course of a surgery. Cables which are not static are also a potential grounding hazard from damage or contact with metal objects they contact inadvertently. Powered devices with active electrical delivery purposes can be inadvertently powered when not in use by a surgeon or other user or in the active surgical space, causing a potential hazard to the patient, the surgeon, the operating room staff, and operating room equipment. Devices with cables can also be cumbersome for cleaning, increasing sterile processing time (if applicable) and increasing set up time.

While the current suite of powered surgical instruments are still tethered, there are major improvements made with battery technology. While ameliorating the cable issues, battery powered devices often fight with battery reliability problems as well as runtime issues. Often times, a battery simply does not last long enough to support a full procedure. Moreover, a battery does not solve inadvertent powering when not in use or in the active surgical space. Additionally, devices that are battery powered have an increased weight and can lead to ergonomic issues for the health care provider, such as no optimal balance of the surgical instrument and/or more rapid fatigue in holding the instrument.

Using wireless energy transfer to power surgical instruments can be problematic because the coil sizes needed to transfer over 10 W of power over a 1-2 foot gap would be relatively large and could interfere with normal surgical instrument operation. Boom arms and other elements needed to keep the gap constant could interfere with the surgeon during a procedure. Additionally, during a procedure, the surgical instrument is moved and positioned in various orientations, making it difficult to maintain a consistent gap and orientation between coils.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the subject matter can be used to power a device, such as, for instance, a surgical device, without the need to tether the device using a power cord or attach a battery to the device. In various examples, the system can reduce the number of trip hazards in the surgical area or other area of use by reducing the number of cords present. The present inventors have recognized the present subject matter can be used to create a balanced, ergonomic device by eliminating uneven weight distribution due to a battery and/or pull from the weight of a cord. To better illustrate the systems described herein, a non-limiting list of examples is provided here:

Example 1 can include subject matter that can include a system for wirelessly transmitting power using resonant magnetic field power transfer. The system includes a device including at least one component to be wirelessly powered. The device includes an elongate shaft and a capture element including a capture coil. A source element wirelessly supplies power to the device. The source element includes a source coil disposed around an opening. The opening is sized to allow the elongate shaft of the device to fit therein. The source coil is located proximate a surgical access point, wherein, with insertion of the elongate shaft within the opening of the source for surgical access. The capture coil is disposed sufficiently proximate the source coil to allow power to be wirelessly transmitted from the source coil to the capture coil to power the at least one component of the device.

In Example 2, the subject matter of Example 1 is optionally configured such that the capture coil is disposed within the elongate shaft of the device.

In Example 3, the subject matter of any one of Examples 1-2 is optionally configured such that the capture coil is disposed within a slider that translates along the elongate shaft of the device.

In Example 4, the subject matter of any one of Examples 1-3 is optionally configured such that the capture coil is disposed within a handle of the device disposed at a proximal end of the elongate shaft of the device.

In Example 5, the subject matter of any one of Examples 1-4 is optionally configured such that the capture coil includes a conductive material having a resistivity lower than $12 \times 10^{-8}$ ohm-meters, the capture element including a first capture layer including a material having a skin depth that is less than a thickness of the first capture layer; a second capture layer including a material having a relative permeability greater than 80 at a resonant frequency; and a third capture layer including a non-conductive material, wherein the capture coil is disposed between the second capture layer and third capture layer.

In Example 6, the subject matter of any one of Examples 1-5 is optionally configured such that the source coil includes a conductive material having a resistivity lower than $12 \times 10^{-8}$ ohm-meters, the source element including a first source layer including a material having a skin depth that is less than a thickness of the first source layer; a second source layer including a material having a relative permeability greater than 80 at a resonant frequency; and a third source layer including a non-conductive material, wherein the source coil is disposed between the second source layer and third source layer.

In Example 7, the subject matter of any one of Examples 1-6 is optionally configured such that the source coil includes a solenoid coil.

In Example 8, the subject matter of any one of Examples 1-7 is optionally configured such that the source coil includes a planar coil.

In Example 9, the subject matter of any one of Examples 1-8 is optionally configured such that the at least one component of the device includes an illumination component, wherein the illumination component is configured to at least one of illuminate an area by producing at least one of visible light, infrared spectrum light, and ultraviolet spectrum light; and measure at least one of temperature, distance, and location by producing a visible laser, an infrared spectrum laser, and an ultraviolet spectrum laser.

In Example 10, the subject matter of any one of Examples 1-9 is optionally configured such that the at least one component of the device includes at least one of a data recorder and a data transmitter, wherein the data includes at least one of video data; image data; temperature data; stress data; strain data; pressure data; flow rate data; torque data; motion and acceleration data; machine vision data; and motion capture data.

In Example 11, the subject matter of any one of Examples 1-10 is optionally configured such that the at least one component of the device includes at least one of a cutting and cauterizing component using direct electrical energy; a cutting and cauterizing component using ultrasonic vibrations; a component to activate a rotational motor to rotate a working member; a component to articulate a working member; a component to power actuation of a cutting member; a component to deploy at least one of a staple, a clamp, and an implanted fixation member; and a component to activate a pump.

In Example 12, the subject matter of any one of Examples 1-11 is optionally configured such that the source element is associated with an attachment member configured to attach directly to a patient. The attachment member includes the source coil disposed within the attachment member, wherein the surgical access point is an incision. The attachment member is configured to be placed at the incision so that insertion of the elongate shaft into the incision places the capture coil proximate the source coil to allow power to be wirelessly transmitted from the source coil to the capture coil.

In Example 13, the subject matter of any one of Examples 1-12 is optionally configured such that the source element is associated with an orifice dilator including the source coil disposed within the orifice dilator, wherein the surgical access point is an orifice. The orifice dilator is configured to be placed within the orifice to expand the orifice to facilitate insertion of the elongate shaft of the device into the orifice, wherein insertion of the elongate shaft into the orifice places the capture coil proximate the source coil to allow power to be wirelessly transmitted from the source coil to the capture coil.

In Example 14, the subject matter of any one of Examples 1-13 is optionally configured such that the source element is associated with an access device including the source coil associated with the access device. The access device is disposed within the patient to form the surgical access point, wherein insertion of the elongate shaft into the access device places the capture coil proximate the source coil to allow power to be wirelessly transmitted from the source coil to the capture coil.

In Example 15, the subject matter of Example 14 is optionally configured such that the source coil is disposed within an attachment removably engageable with the access device.

In Example 16, the subject matter of Example 14 is optionally configured such that the source coil is disposed within the access device.

Example 17 can include, or can optionally be combined with any one of Examples 1-16 to include subject matter that can include a system for wirelessly transmitting power using resonant magnetic field power transfer. The system includes a device including at least one component to be wirelessly powered. The device includes an elongate shaft and a capture element including a capture coil. A first capture layer includes a material having a skin depth that is less than a thickness of the first capture layer. A second capture layer includes a material having a relative permeability greater than 80 at a resonant frequency. A third capture layer includes a non-conductive material, wherein the capture coil is disposed between the second capture layer and third capture layer. A source element wirelessly supplies power to the device and includes a source coil. A first source layer includes a material having a skin depth that is less than a thickness of the first source layer. A second source layer includes a material having a relative permeability greater than 80 at a resonant frequency. A third source layer includes a non-conductive material, wherein the source coil is disposed between the second source layer and third source layer. The source coil is disposed around an opening. The opening is sized to allow the elongate shaft of the device to fit therein. The source is located proximate a surgical access point, wherein, with insertion of the elongate shaft within the opening of the source for surgical access, the capture coil is disposed sufficiently proximate the source coil to allow power to be wirelessly transmitted from the source coil to the capture coil to power the at least one component of the device.

In Example 18, the subject matter of Example 17 is optionally configured such that the source element is associated with an attachment member configured to attach directly to a patient. The attachment member includes the source coil disposed within the attachment member, wherein the surgical access point is an incision. The attachment member is configured to be placed at the incision so that insertion of the elongate shaft into the incision places the capture coil proximate the source coil to allow power to be wirelessly transmitted from the source coil to the capture coil.

In Example 19, the subject matter of Example 17 is optionally configured such that the source element is associated with an orifice dilator including the source coil disposed within the orifice dilator, wherein the surgical access point is an orifice. The orifice dilator is configured to be placed within the orifice to expand the orifice to facilitate insertion of the elongate shaft of the device into the orifice, wherein insertion of the elongate shaft into the orifice places the capture coil proximate the source coil to allow power to be wirelessly transmitted from the source coil to the capture coil.

In Example 20, the subject matter of Example 17 is optionally configured such that the source element is associated with an access device including the source coil associated with the access device. The access device is disposed within the patient to form the surgical access point, wherein insertion of the elongate shaft into the access device places the capture coil proximate the source coil to allow power to be wirelessly transmitted from the source coil to the capture coil.

DETAILED DESCRIPTION

Figure 1A:
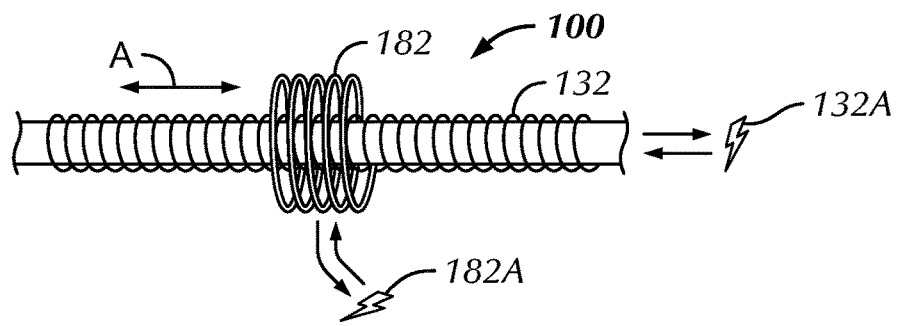
FIG. 1A is a diagrammatic view of a system for wireless power transfer in accordance with at least one example of the invention.
Figure 1B:
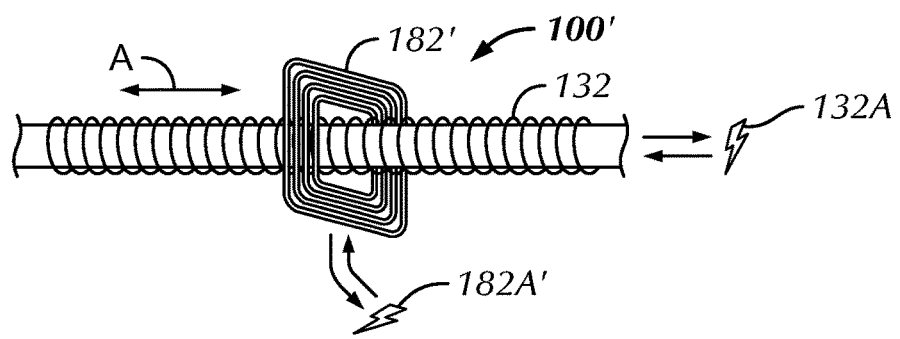
FIG. 1B is a diagrammatic view of a system for wireless power transfer in accordance with at least one example of the invention.
Figure 1C:
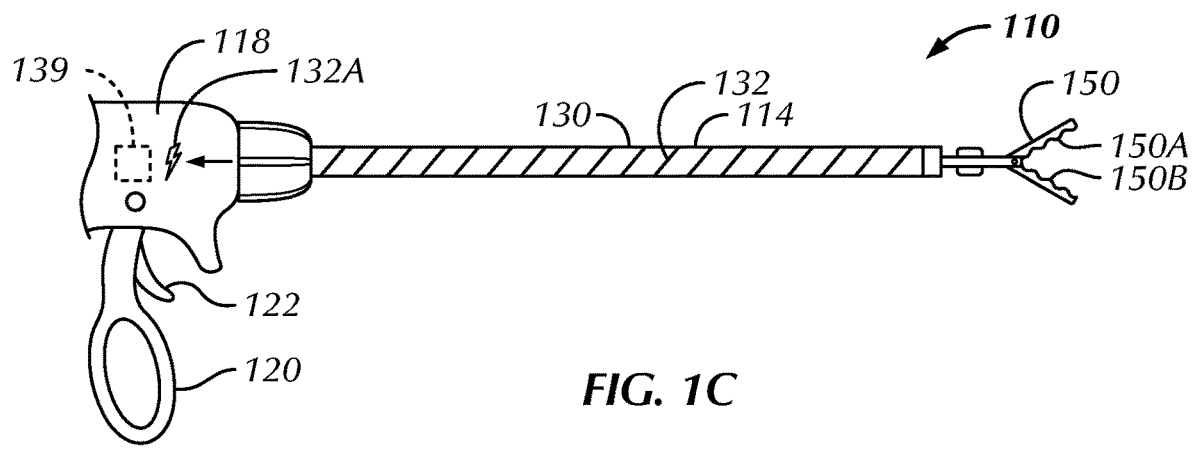
FIG. 1C is a side view of a wirelessly powered device in accordance with at least one example of the invention.

The present patent application relates to a system for wirelessly powering devices used for minimally invasive surgery and procedures. In various examples, as described herein, the system can be used to wirelessly power one or more of various types of instruments used in minimally invasive surgery and/or procedures, thereby potentially eliminating the need for a cord or a battery to supply power to the instrument.

The present subject matter seeks to minimize, if not eliminate, the need for an energy storage device (such as a battery, a super capacitor, or the like) or a tether cord to the instrument. By eliminating a tethered cord from an instrument, any pull on the instrument resulting from the weight of a cord can be eliminated. Eliminating a cord from an instrument can also help reduce tripping hazards as the instrument will no longer include a cord that changes location with movement and/or use of the instrument. In some examples, when the instrument is not in the surgical space, the instrument will not receive power, so there is little to no danger that an instrument that is inadvertently left on will cause injury or damage. In some examples, the wirelessly powered device has no potential or transmittable energy, thereby increasing the safety of the instrument in the surgical suite. Additionally, by being wirelessly powered, a physician, dentist, or other user can feel relatively confident that the instrument will perform properly for the entire procedure in that there is no battery that will fail unexpectedly or not last an entire procedure. By delivering power to the surgical instrument wirelessly, the surgical instrument can run continuously without the need to replace a battery and without restrictions that a cord on a surgical instrument would provide.

A relatively high amount of power can be sent to a surgical instrument because orientation and position of the surgical instrument do not affect energy transfer since, in some examples, a capture element of the surgical instrument passes through or proximate the center of a source element. Since a shaft of the instrument has to be inserted through an opening in the patient for a surgical, dental, or other procedure, a capture coil of the capture element can maintain a close proximity and alignment to a source coil of the source element during the procedure. This is further improved by the uniformity of magnetic fields within solenoids, allowing for further diameter and alignment mismatch between the source coil and the capture coil.

In various examples, the system described herein can be implemented in a broad range of medical or other applications to power currently powered devices used in procedures and enable power in devices that currently are not powered.

In some examples, the present system can be used with endoscopic surgical instruments, which generally include a narrow shaft insertable through a port into an internal surgical working space. Some examples of endoscopic procedures where an access device source can be used include, but are not limited to: through the mouth (such as, but not limited to, bronchoscopy, enteroscopy, laryngoscopy, and dental procedures); through the nose (such as, but not limited to, eronchoscopy, laryngoscopy, and ureteroscopy); through the anus (such as, but not limited to, colonoscopy and enteroscopy); through the urethra (such as, but not limited to, cystoscopy); through the vagina (such as, but not limited to, hysteroscopy); through an abdominal incision (such as, but not limited to, laparoscopy); through a chest incision (such as, but not limited to, mediastinoscopy); through an incision at a joint (such as, but not limited to, arthroscopy); and through an incision in the skull (such as, but not limited to, keyhole craniotomies).

In some examples, the present system can be used with endovascular and/or interventional cardiology and/or radiology procedures, which typically use catheters going through a percutaneous access device into major arteries for the respective procedure. Some examples of such procedures include, but are not limited to: cardiovascular stent placement; catheter directed thrombosis; tissue ablation (such as, but not limited to, radiofrequency, microwave, cryo, irreversible electroporation, and high-intensity focused ultrasound); blocking cardiovascular blood supply (such as, but not limited to, trans-arterial chemoembolization); procedures through percutaneous spinal incisions (such as, but not limited to, vertebroplasty and kyphonoplasty); catheterized biopsies; and renal procedures and dialysis.

While the following describes the system with respect to certain example devices, it is not intended to be so limited. In various examples, the system can be used with various devices, including devices to be used with the above-listed example procedures, as well as other devices used in procedures not specifically listed.

The following co-owned applications relate to wireless power transmission and are hereby incorporated by reference in their entireties: U.S. application Ser. No. 14/602,828, now U.S. Pat. No. 9,842,686, filed Jan. 22, 2015 and entitled "SPLIT WINDING REPEATER"; U.S. application Ser. No. 14/170,945, now U.S. Pat. No. 9,755,456, filed Feb. 3, 2014 and entitled "CONTROL CIRCUIT FOR WIRELESS POWER"; and U.S. application Ser. No. 15/055,063, now U.S. Patent Application Publication No. 2016/0254694, filed Feb. 26, 2016 and entitled "BATTERY WIRELESS CHARGING SYSTEM".

Generally, the present subject matter, in some examples, includes a source coil for transmitting electrical power located within an access device and/or at or near an access point of a procedure. In various examples, the source coil can at least partially encircle, either as a planar coil or as a solenoid, the access point where a device to be powered can pass through. A receiving or capture coil, in some examples, can be located on or within the device. In some examples, the capture coil can be located on, within, or proximate a shaft of the device, which can pass through an inner diameter of the source coil for the access point of the procedure. In some examples, the capture coil can be oriented by a solenoid along more of the shaft than is captured within the source at any one time, or a specific location, locked in position and orientation to the source coil. Such a configuration, in various examples, makes substantially constant a distance or minimizes a changing distance between the coils by having the source coil located at or near the surgical access point. Additionally, such a configuration, in various examples, makes substantially constant an orientation or minimizes a changing orientation between the coils so magnetic fields of the coils are receptive to each other. This can be done through mechanical concentric alignment and/or uniform magnetic fields created by the solenoid.

The present subject matter, in some examples, allows for multiple outside-diameter-sized devices to be inserted through a single inside-diameter source, allowing for a variety of offset axis and inside-diameter-to-outside-diameter distances. In various example, the present subject matter can regulate power to be utilized by the medical device, for instance, for use by one or more sensors, one or more user interfaces, and/or one or more motors. When used in an electrosurgical application, in some examples, control and regulation can occur within the device.

The present subject matter includes various placements of the capture coil. Nearly all minimally invasive, endoscopic and intravenous surgical instruments utilize a narrow shaft going through an opening into an internal surgical working space, meaning the various example systems described herein can bring power to any type of instrument or device working through a restricted opening into a patient. During a given procedure, the device will need to translate linearly along its axis and/or rotate about its axis, and the axis may deviate angularly from orthogonal to the surgical surface of entry. Applicable devices include, for instance, visualization scopes, currently-corded powered instruments, currently-battery-powered instruments, currently-unpowered instruments which could be powered for mechanical or electrical advantage, added sensors to devices currently with or without power, and many other devices not directly specified.

The present subject matter, in various examples, includes transmitting electrical power via a resonant source coil, encapsulating within its inner diameter, a receiver coil which can receive power while translating linearly, rotating about its axis, changing the angle versus the tangent of the patient surface, and changing axis center-to-center misalignment. As the receiver coil actively moves in the ways mentioned above through the field during use, (linearly through the transmission coil, distance between coil axis and offset between axis parallelism), the inductance of the source coil fluctuates, which, in turn, causes the resonant frequency to shift. This is due to the presence of metal from the shaft, ferrite added to the shaft, and/or the inductor on the shaft. One solution to resolve this is to simply tune the resonant frequency with the capture inductor assembly present in the source coil. This now means the source coil detunes when the capture coil is not present. There is no need to have the source active when there is no device present; having the source disabled, except when the capture coil is present, resolves the issue of the coil no longer being resonant because the device is not functioning. Adaptively adjusting the impedance matching network components, such as the capacitor values, while the inductance change is occurring can maintain the targeted resonant frequency. Utilizing a slider mechanism minimizes the inductance fluctuations during active motion described above and between different devices of different diameters utilized within the source.

The capture coil can be contained within the shaft of instruments and devices, as described in various examples below. In this way, the capture coil can be on the same axis as and located on the minimally invasive surgical shaft. This area can be shielded and only along the length where it will interact with the source when the device is in the functional workspace. At any point, only part of the capture coil will be covered by the source coil. Energy is transferred equally at all points of insertion into the working space. The magnetic field which is generated by the solenoidal source will be uniform within the inner diameter, where the capture coil can receive. The impedance matching components can be adjusted to maintain the targeted resonant frequency as the inductance shifts. The values change is done to maintain the specific R+jX impedances as designed and also satisfy the resonant formula of $f=(2\pi(LC)^{1/2})^{-1}$.

In some examples, as described in various examples below, the capture coil can be placed in a sliding collar or slider around the shaft which would contact and maintain a constant distance with the source coil but not enter the port attachment or go through the opening within the source configuration. As the instrument is advanced or retracted though the port or opening, the slider with the capture coil slides proximally in relation to the instrument, thereby maintaining a constant distance with the source coil configurations. This maintains the resonant impedance while allowing the device mobility as described above.

Getting power using magnetic fields using high resonance requires two inductor coils for transmitting the energy and receiving the energy. The transmitter is a source coil and the receiving coil is a capture coil. In order for the source coil to transfer energy to the capture coil, a magnetic field needs to be generated by passing a current through the source coil. If a capture coil is then placed within that magnetic field, that field will induce a current into the coil. Current through a wire creates a magnetic field and the opposite is also true in that a magnetic field around a wire will induce a current. High resonance involves sending an AC signal through a source coil that is resonant at the same frequency of the signal. This reduces the losses within the coil. A capture device that is also tuned to the same resonant frequency also has lower losses and, as such, needs less of a magnetic field in order to receive the same amount of power since the coil losses are greatly reduced.

Simply placing a coil within a magnetic field, however, does not necessarily mean the magnetic field will induce a current. The distance the magnetic field travels is a function of the coil diameter. The larger the diameter of the coil, the longer the distance the magnetic field can travel. In some examples, source coils are larger than the capture device since normally the capture device is held while the source is placed somewhere else.

The present subject matter relies on the idea that the capture coil does not need a uniform magnetic field induced on all parts of the capture coil, but rather only a part of the capture coil. As an example, having a 24" tall capture coil inserted into a planar type or a solenoid coil source coil that is 0.5" tall will still transfer energy. The magnetic field from the source will induce a current on several winding of the longer capture coil. This, in turn, creates a current which flows through the entire coil, which then ultimately creates a magnetic field around the rest of the coil. In some examples, since the source coil is a planar coil or a solenoid, or goes around the source, the surgical instrument can be rotated 360 degrees about the shaft without any major changes to the energy transfer. Also, in some examples, the surgical instrument cannot angle far enough to cause the energy transfer to cease as the coils cannot become perpendicular to each other while the shaft is inserted. Furthermore, if a mechanical housing is needed as part of the surgery, such housing will further restrict angular movement of the surgical instrument.

In some examples, if windings of the capture coil on the shaft over any area include the same pitch and the same number of turns, the voltage will stay relatively static as the shaft and, in turn, the capture coil, passes through the source coil. In this example, because the shaft and, in turn, the capture coil, and the source coil are close to each other, the source coil can be disposed around the shaft, and the shaft is inserted into the source coil as part of the surgery, the distance between the capture coil and the source coil can be largely constrained in the X,Y dimension. By making the capture coil the entire length of the shaft, the Z dimension is also constrained as, once inserted, the voltage will be roughly the same no matter what part of the shaft is inserted into the source. There can be some voltage changes as the shaft is first inserted into the source coil as more of the magnetic field reaches more windings on the shaft; however, once it has reached the maximum k factor (coupling factor—percentage of magnetic field from the source that interacts with the capture coil), the voltage will stabilize.

In some examples, because the source coil has to create a large magnetic field for energy to be transferred, the magnetic field will be the strongest between the capture coil and source coil as the field will concentrate between the two coils. There are fields everywhere, but the source coil field can be shielded so that it is confined only within the space between the shaft and the source coil. The shaft can have a field created around it entirely once a current is induced; however, that field can be low enough to meet all applicable safety standards.

In various examples, the present subject matter includes various placements and orientations of the source coil based on the types of access needed in each procedure. Four general access types include introducer access (where ports are used as access devices, such as arthroscopic guides, laparoscopic ports, and mediastinoscopy ports, for instance); percutaneous/trans-arterial (introducer) access (where introducer ports are used as access devices, such as for interventional cardiovascular procedures, for instance); incision access (where no access device is typically used (such as in arthroscopy and keyhole craniotomies, for instance); and orifice access (where access is done through an orifice, either not utilizing an access device or using an access device for dilating the orifice).

With the above general concepts in mind, more specific examples are now described. The following examples of systems for wirelessly transmitting power using resonant magnetic field power transfer implement one or more of the concepts discussed above.

Referring to FIGS. 1A-3C, in various examples, various systems 100, 100', 200, 200', 300, 300' for wirelessly transmitting power using resonant magnetic field power transfer can be seen. In some examples, the system 100, 100', 200, 200', 300, 300' includes a device 110, 210, 310 including at least one component 150, 250 to be wirelessly powered. For instance, as shown in FIG. 1C, in some examples, the component 150 can include a laparoscopic gripper 150 including jaws 150A, 150B to be powered. In other examples, as shown in FIG. 2C, the component 250 to be powered can include an arthroscopic burr 250. In some examples, the device 110, 210, 310 can include control circuitry which is wirelessly powered and then, in turn, controls the component 150, 250. In some examples, the device 110, 210, 310 includes an elongate shaft 114, 214, 314 and a capture element 130, 230, 330 including a capture coil 132, 232, 332. In various examples, the device 110, 210, 310 can include any of various types of devices, including, but not limited to, a medical device and/or a dental device, for instance, for use in one of the above-listed procedures. While various exemplary devices are shown and described herein, these are merely exemplary and should not be considered limiting.

In some examples, the system 100, 100', 200, 200', 300, 300' includes a source element (described in more detail below) for wirelessly supplying power to the device 110, 210, 310. In some examples, the source element includes a source coil 182, 182', 282, 282', 382, 382' disposed proximate an opening of the source element. In some examples, the source coil 182, 182', 282, 282', 382, 382' is disposed around the opening. The opening can be sized to allow the elongate shaft 114, 214, 314 of the device 110, 210, 310 to fit therein. In some examples, the source coil 182, 182', 282, 282', 382, 382' is located proximate a surgical access point, wherein, with insertion of the elongate shaft 114, 214, 314 within the opening of the source element for surgical access, the capture coil 132, 232, 332 is disposed sufficiently proximate the source coil 182, 182', 282, 282', 382, 382' to allow power to be wirelessly transmitted from the source coil 182, 182', 282, 282', 382, 382' to the capture coil 132, 232, 332 to power the at least one component 150, 250 of the device 110, 210, 310.

Referring specifically to FIGS. 1A-1E, in some examples, the capture element 130 of the device 110 can be disposed within the elongate shaft 114, such that passing at least a portion of the shaft 114 through or proximate the source coil 182, 182' allows for the wireless transfer of power from the source coil 182, 182' to the capture coil 132. In some examples, the source coil 182 can include a solenoid coil 182. In other examples, the source coil 182' can include a planar coil 182'. Depending upon the configuration of the source element, either the solenoid coil 182 or the planar coil 182' can be used. For instance, in some examples, in a substantially flat source element, the planar coil 182' can be used. In other examples, in a more tubular source element, the solenoid coil 182 can be used. In some examples, with the capture element 130 running along a length of the shaft 114, the shaft 114 of the device 110 can be moved along arrow A with respect to the source coil 182, 182' while still maintaining the capture coil 132 proximate the source coil 182, 182', thereby allowing for power transfer from the source coil 182, 182' to the capture coil 132 at a range of locations of the elongate shaft 114 with respect to the source coil 182, 182'. That is, in some examples, the device 110 and, in turn, the elongate shaft 114 can be moved along arrow A without interrupting power transfer from the source coil 182, 182' to the capture coil 132.

In some examples, the source coil 182, 182' receives power 182A, 182A', for instance, from being plugged into an electrical outlet or otherwise supplied with power. With the shaft 114 of the device 110 disposed within or otherwise proximate the source coil 182, 182', in some examples, the power 182A, 182A' can be wirelessly transferred from the source coil 182, 182' to the capture coil 132 to supply power 132A to the device 110. In some examples, the capture coil 132 is electrically coupled directly to the component 150, such that the power 132A is supplied directly to the component 150. In other examples, the capture coil 132 is electrically coupled to control circuitry 139, such that the power 132A is supplied to the control circuitry 139 to power and control the component 150. In some examples, the control circuitry 139 is disposed within a handle 118 of the device 110. In some examples, the elongate shaft 114 extends outwardly from the handle 118. In some examples, a physician or other user can control the component 150 using a control 120. The control 120, in various examples, can be disposed on or extend from the handle 118. In some examples, the device 110 includes more than one control 120, 122 to control different aspects of the component 150. For instance, with respect to the example shown in FIG. 1C, the device 110 can include a first control 120 to operate (for instance, close and/or open) jaws 150A, 150B of a gripper 150. In some examples, the device 110 can further or alternatively include a second control 122 to operate (for instance, turn on and/or turn off) a cauterizer, a stapler, or the like.

In some examples, the capture coil 132 includes a conductive material having a resistivity lower than $12 \times 10^{-8}$ ohm-meters. In some examples, the capture coil 132 can include one or more of copper, aluminum, or the like.

Figure 1D:
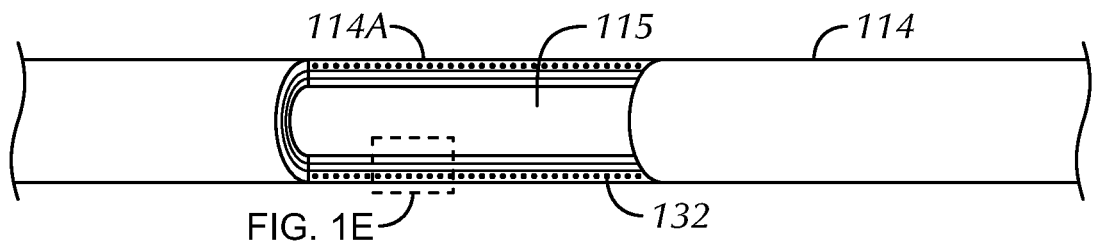
FIG. 1D is a partially cut-away side view of an elongate shaft of a wirelessly powered device in accordance with at least one example of the invention.
Figure 1E:
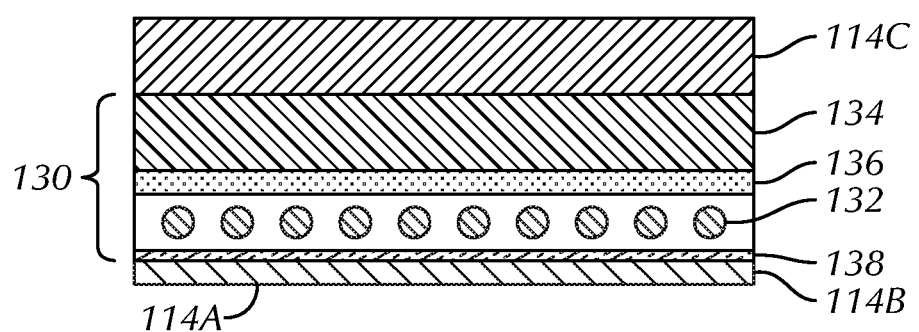
FIG. 1E is an enlarged cross-sectional view of the elongate shaft of the wirelessly powered device of FIG. 1D.

Referring specifically to FIGS. 1D and 1E, in some examples, the capture element 130 is associated with the elongate shaft 114 of the device 110. In further examples, the capture element 130 is disposed within the elongate shaft 114 of the device 110. In still further examples, the capture element 130 is disposed within a sidewall 114A of the elongate shaft 114. In some examples, the capture element 130 is disposed between an outer layer 114B and an inner layer 114C of the sidewall 114A. The materials of the outer layer 114B and the inner layer 114C can vary, in various examples, depending upon the application for the device 100. For instance, in some examples, the outer layer 114B can include a lubricious layer or coating to facilitate insertion of the device 110 within, for instance, a patient. In some examples, the inner layer 114C can include a structurally rigid material or component in order to give the elongate shaft 114 rigidity. In some examples, one or both of the outer layer 114B and the inner layer 114C can include multiple layers depending upon the application for the device 110. In other examples, the elongate shaft 114 can include just one of the outer layer 114B or the inner layer 114C. In still other examples, the elongate shaft 114 need not include either of the outer layer 114B or the inner layer 114C, instead relying on the capture element 130 to form the sidewall 114A of the elongate shaft 114.

In some examples, the capture element 130 includes various layers in addition to the capture coil 132. For instance, in some examples, the capture element 130 includes a first capture layer 134 including a material having a skin depth that is less than a thickness of the first capture layer 134. In some examples, the first capture layer 134 is a material with a relatively high conductivity. The first capture layer 134, in some examples, is an innermost layer of the capture element 130. In some examples, the first capture layer 134 can include one or more of copper, aluminum, or the like. In some examples, the capture element 130 includes a second capture layer 136 including a material having a relative permeability greater than 80 at a particular frequency or frequency range. In some examples, the second capture layer 136 includes a material having a relative permeability greater than 80 at a resonant frequency for the system 100, 100'. The second capture layer 136, in some examples, abuts and is disposed outwardly from the first capture layer 134 of the capture element 130. In some examples, the second capture layer 136 can include ferrite. In further examples, the second capture layer 136 can include FJ7 ferrite. In some examples, the capture element 130 includes a third capture layer 138 including a non-conductive material. In some examples, the third capture layer 138 can be used as to insulate the capture coil 132 from the outer layer 114B of the shaft 114 and/or the exterior of the shaft 114. The third capture layer 138, in some examples, is an outermost layer of the capture element 130. In some examples, the third capture layer 138 can include one or more of a polyether ether ketone (PEEK) material, a polytetrafluoroethylene (PTFE) material, a polyolefin material, or the like. The capture coil 132, in some examples, can be disposed between the second capture layer 136 and third capture layer 138. In other examples, the capture coil 132 and the first, second, and third layers 134, 136, 138 of the capture element 130 can be differently disposed or otherwise arranged, provided the capture element 130 can function to wirelessly capture the field created by the source coil 182, 182' of the source element.

In some examples, the elongate shaft 114 includes a lumen 115 therethrough. The lumen 115, in various examples, can be used to run various components, conduits, or the like. For instance, in some examples, one or more wires (electrical, fiber optic, data, etc.) can extend through the lumen 115 from the control circuitry 139 to the component 150. In other examples, one or more conduits can extend within the lumen 115 in order to transport fluids (such as various gases, liquids, and/or other substances) to and/or from a distal end of the elongate shaft 114. In further examples, depending upon the component 150 used with the device 110, various mechanical components can extend within the lumen 115, such as, but not limited to, a rotational and/or translational shaft, a linkage, one or more pullwires, or the like. In still further examples, wires (electrical, fiber optic, data, etc.) for one or more of various other components can be run within the lumen 115 of the elongate shaft 114, such as, but not limited to, one or more sensors, one or more cameras, one or more lights, one or more lasers, or a combination thereof. In some examples, it should be understood that a combination of two or more of the above-listed examples of wires, conduits, components, etc. can be included within the lumen 115 of the elongate shaft 114, depending upon the application for the device 110.

Figure 2A:
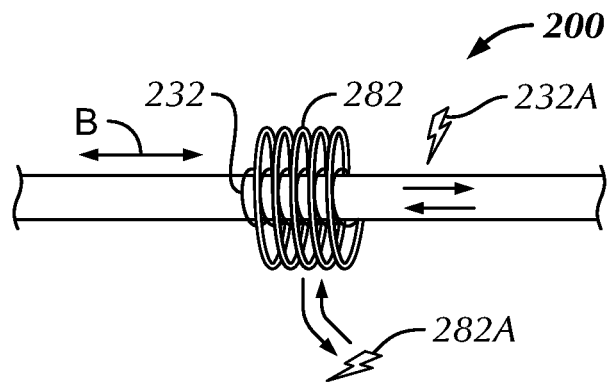
FIG. 2A is a diagrammatic view of a system for wireless power transfer in accordance with at least one example of the invention.
Figure 2B:
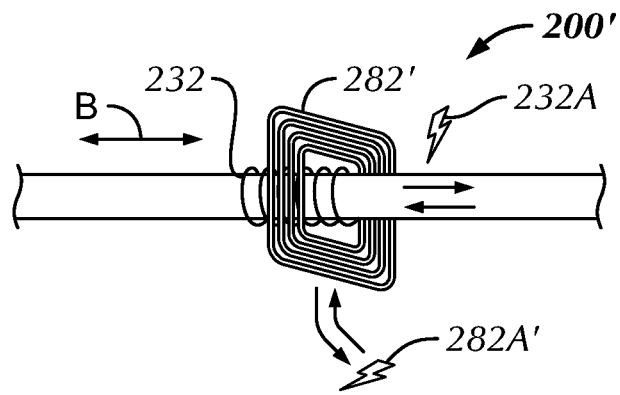
FIG. 2B is a diagrammatic view of a system for wireless power transfer in accordance with at least one example of the invention.
Figure 2C:
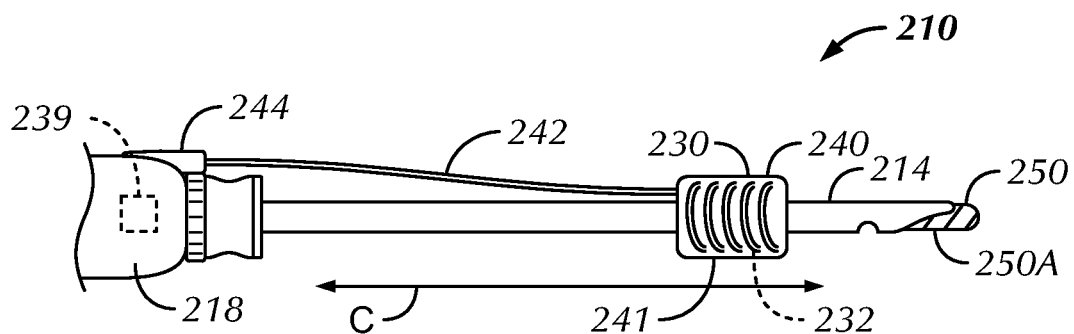
FIG. 2C is a side view of a wirelessly powered device in accordance with at least one example of the invention.

Referring to FIGS. 2A-2C, in some examples, the capture element 230 of the device 210 can be disposed within a slider 240 translatable (arrow C) along the elongate shaft 214 of the device 210, such that having the slider 240 disposed proximate the source coil 282, 282' allows for the wireless transfer of power from the source coil 282, 282' to the capture coil 232. In some examples, the source coil 282 can include a solenoid coil 282. In other examples, the source coil 282' can include a planar coil 282'. Depending upon the configuration of the source element, either the solenoid coil 282 or the planar coil 282' can be used. For instance, in some examples, in a substantially flat source element, the planar coil 282' can be used. In other examples, in a more tubular source element, the solenoid coil 282 can be used. In some examples, with the capture element 230 slidable along a length of the shaft 214, the shaft 214 of the device 210 can be moved along arrow B with respect to the source coil 282, 282' while still maintaining the capture coil 232 proximate the source coil 282, 282', thereby allowing for power transfer from the source coil 282, 282' to the capture coil 232 at a range of locations of the elongate shaft 214 with respect to the source coil 282, 282'. That is, in some examples, the device 210 and, in turn, the elongate shaft 214 can be moved along arrow B without interrupting power transfer from the source coil 282, 282' to the capture coil 232.

In some examples, the source coil 282, 282' receives power 282A, 282A', for instance, from being plugged into an electrical outlet or otherwise supplied with power. With the slider 240 of the device 210 disposed within or otherwise proximate the source coil 282, 282', in some examples, the power 282A, 282A' can be wirelessly transferred from the source coil 282, 282' to the capture coil 232 to supply power 232A to the device 210. In some examples, the capture coil 232 is electrically coupled directly to the component 250, such that the power 232A is supplied directly to the component 250. In other examples, the capture coil 232 is electrically coupled to control circuitry 239, such that the power 232A is supplied to the control circuitry 239 to power and control the component 250. In some examples, the control circuitry 239 is disposed within a handle 218 of the device 210. In some examples, the elongate shaft 214 extends outwardly from the handle 218, with the slider 240 sliding along the elongate shaft 214. In some examples, a tether 242 extends between a retractor 244 and the slider 240. In some examples, the tether 242 includes a wire electrically coupling the capture coil 232 within the slider 240 back to the handle 218 to then be electrically coupled to the control circuitry 239 and/or the component 250. In some examples, the retractor 244 allows for extension of the tether 242, for instance, when the slider 240 is moved distally along the elongate shaft 214, and for retraction of the tether 242, for instance, when the slider 240 is moved proximally along the elongate shaft 214. In this way, the tether 242 can be maintained relatively taut and/or close to the shaft 214 and/or handle 218 of the device 210, thereby decreasing the chances that the tether 242 gets snagged or otherwise caught up by an object or person during use.

In some examples, a physician or other user can control the component 250 using a control. The control, in various examples, can be disposed on or extend from the handle 218. In some examples, the device 210 includes more than one control to control different aspects of the component 250. For instance, with respect to the example shown in FIG. 2C, the device 210 can include a first control to operate (for instance, rotate) a burr member 250A of a burr 250. In some examples, the device 210 can further or alternatively include a second control to operate (for instance, turn on and/or turn off) suction, saline, or the like.

In some examples, the capture element 230 is associated with the slider 240 of the device 210. In further examples, the capture element 230 is disposed within the slider 240 of the device 210. In some examples, the capture element 230 is substantially similar to the capture element 130 described above except that the capture element 230 is associated with the slider 240. In some examples, the capture element 230 is disposed proximate an exterior surface of the slider 240. In some examples, the capture element 230 is disposed within a housing 241 of the slider 240. In addition to the capture element 230, the slider 240 can also include space within the housing 241, for instance, to house components in addition to the capture element 230, such as, but not limited to electronic modules or other components, wiring, or the like.

In some examples, the capture element 230 includes various layers similar to those described above with respect to the capture element 130. In some examples, the capture coil 232 includes a conductive material having a resistivity lower than $12 \times 10^{-8}$ ohm-meters. In some examples, the capture coil 232 can include one or more of copper, aluminum, or the like. In some examples, the capture element 230 includes a first capture layer including a material having a skin depth that is less than a thickness of the first capture layer. In some examples, the first capture layer is a material with a relatively high conductivity. The first capture layer, in some examples, is an innermost layer of the capture element 230. In some examples, the first capture layer can include one or more of copper, aluminum, or the like. In some examples, the capture element 230 includes a second capture layer including a material having a relative permeability greater than 80 at a particular frequency or frequency range. In some examples, the second capture layer includes a material having a relative permeability greater than 80 at a resonant frequency for the system 200, 200'. The second capture layer, in some examples, abuts and is disposed outwardly from the first capture layer of the capture element 230. In some examples, the second capture layer can include ferrite. In further examples, the second capture layer 136 can include FJ7 ferrite. In some examples, the capture element 230 includes a third capture layer including a non-conductive material. In some examples, the third capture layer can be used as to insulate the capture coil 232 from the housing 241 of the slider 240. The third capture layer, in some examples, is an outermost layer of the capture element 230. In some examples, the third capture layer can include one or more of a polyether ether ketone (PEEK) material, a polytetrafluoroethylene (PTFE) material, a polyolefin material, or the like. The capture coil 232, in some examples, can be disposed between the second capture layer and third capture layer. In other examples, the capture coil 232 and the first, second, and third layers of the capture element 230 can be differently disposed or otherwise arranged, provided the capture element 230 can function to wirelessly capture the field created by the source coil 282, 282' of the source element.

In some examples, the elongate shaft 214 includes a lumen therethrough similar to the lumen 115 described above with respect to the device 110. The lumen, in various examples, can be used to run various components, conduits, or the like. For instance, in some examples, one or more wires (electrical, fiber optic, data, etc.) can extend through the lumen from the control circuitry 239 to the component 250. In other examples, one or more conduits can extend within the lumen in order to transport fluids (such as various gases, liquids, and/or other substances) to and/or from a distal end of the elongate shaft 214. In further examples, depending upon the component 250 used with the device 210, various mechanical components can extend within the lumen, such as, but not limited to, a rotational and/or translational shaft, a linkage, one or more pullwires, or the like. In still further examples, wires (electrical, fiber optic, data, etc.) for one or more of various other components can be run within the lumen of the elongate shaft 214, such as, but not limited to, one or more sensors, one or more cameras, one or more lights, one or more lasers, or a combination thereof. In some examples, it should be understood that a combination of two or more of the above-listed examples of wires, conduits, components, etc. can be included within the lumen of the elongate shaft 214, depending upon the application for the device 210.

Figure 3A:
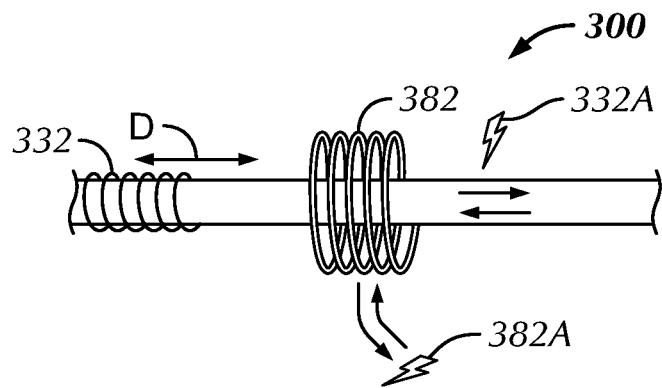
FIG. 3A is a diagrammatic view of a system for wireless power transfer in accordance with at least one example of the invention.
Figure 3B:
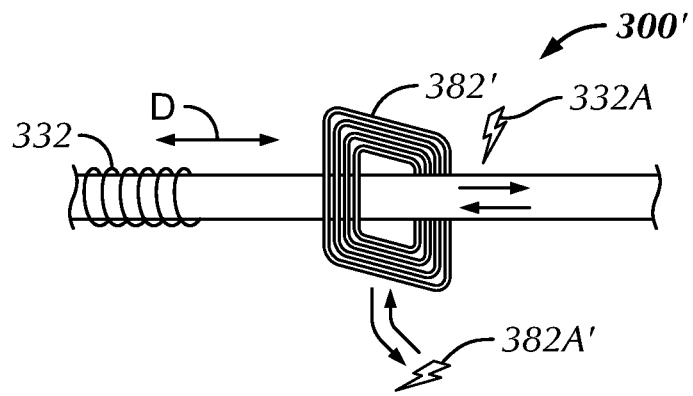
FIG. 3B is a diagrammatic view of a system for wireless power transfer in accordance with at least one example of the invention.
Figure 3C:
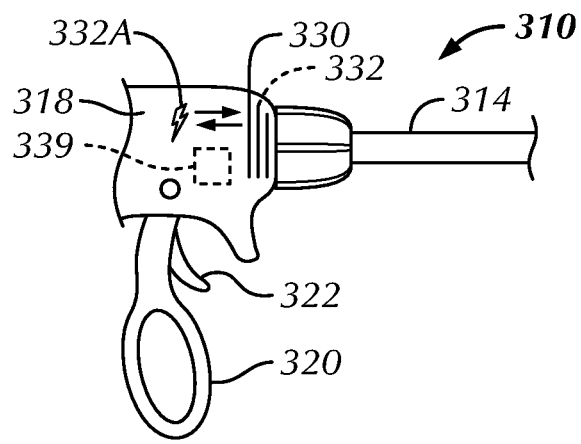
FIG. 3C is a side view of a wirelessly powered device in accordance with at least one example of the invention.

Referring to FIGS. 3A-3C, in some examples, the capture element 330 of the device 310 can be associated with a handle 318 of the device 310, such that, with the handle 318 proximate the source coil 382, 382', power can be wirelessly transferred from the source coil 382, 382' to the capture coil 332. In some examples, the capture element 330 of the device 310 can be disposed within the handle 318 of the device 310. In further examples, the capture element 330 is disposed within the handle 318 of the device 310, the handle being disposed at a proximal end of the elongate shaft 314 of the device 310. In some examples, the source coil 382 can include a solenoid coil 382. In other examples, the source coil 382' can include a planar coil 382'. Depending upon the configuration of the source element, either the solenoid coil 382 or the planar coil 382' can be used. For instance, in some examples, in a substantially flat source element, the planar coil 382' can be used. In other examples, in a more tubular source element, the solenoid coil 382 can be used. In some examples, with the capture element 330 associated with the handle 318, the shaft 314 of the device 310 can be moved along arrow D with respect to the source coil 382, 382' while still maintaining the capture coil 332 proximate the source coil 382, 382', thereby allowing for power transfer from the source coil 382, 382' to the capture coil 332 at a range of locations of the elongate shaft 314 with respect to the source coil 382, 382'. That is, in some examples, the device 310 and, in turn, the elongate shaft 314 can be moved along arrow D without interrupting power transfer from the source coil 382, 382' to the capture coil 332.

In some examples, the source coil 382, 382' receives power 382A, 382A', for instance, from being plugged into an electrical outlet or otherwise supplied with power. With the handle 318 of the device 310 disposed proximate the source coil 382, 382', in some examples, the power 382A, 382A' can be wirelessly transferred from the source coil 382, 382' to the capture coil 332 to supply power 332A to the device 310. In some examples, the capture coil 332 is electrically coupled directly to a component of the device 310, such that the power 332A is supplied directly to the component. In other examples, the capture coil 332 is electrically coupled to control circuitry 339, such that the power 332A is supplied to the control circuitry 339 to power and control the component. Although not shown, the component of the device 310 can include any powered component for the device 310 for minimally invasive surgery, such as, but not limited to one or more of a gripper, a burr, a camera, a light, a laser, a sensor, a cutter, a cauterizer, a drill, etc. In some examples, the control circuitry 339 is disposed within the handle 318 of the device 310.

In some examples, a physician or other user can control the component using a control 320. The control 320, in various examples, can be disposed on or extend from the handle 318. In some examples, the device 310 includes more than one control 320, 322 to control different aspects of the component. Various configurations of the device 310 and control thereof are contemplated herein, depending upon the application of the device 310.

In some examples, the capture element 330 is associated with the handle 318 of the device 310. In further examples, the capture element 330 is disposed within the handle 318 of the device 310. In some examples, the capture element 330 is substantially similar to the capture elements 130, 230 described above except that the capture element 330 is associated with the handle 318. In some examples, the capture element 330 is disposed proximate an exterior surface of the handle 318. In addition to the capture element 330, the handle 318 can also include space within the handle 318, for instance, to house components in addition to the capture element 330, such as, but not limited to electronic modules or other components, wiring, or the like.

In some examples, the capture element 330 includes various layers similar to those described above with respect to the capture elements 130, 230. In some examples, the capture coil 332 includes a conductive material having a resistivity lower than $12 \times 10^{-8}$ ohm-meters. In some examples, the capture coil 332 can include one or more of copper, aluminum, or the like. In some examples, the capture element 330 includes a first capture layer including a material having a skin depth that is less than a thickness of the first capture layer. In some examples, the first capture layer is a material with a relatively high conductivity. The first capture layer, in some examples, is an innermost layer of the capture element 330. In some examples, the first capture layer can include one or more of copper, aluminum, or the like. In some examples, the capture element 330 includes a second capture layer including a material having a relative permeability greater than 80 at a particular frequency or frequency range. In some examples, the second capture layer includes a material having a relative permeability greater than 80 at a resonant frequency for the system 300, 300'. The second capture layer, in some examples, abuts and is disposed outwardly from the first capture layer of the capture element 330. In some examples, the second capture layer can include ferrite. In further examples, the second capture layer 136 can include FJ7 ferrite. In some examples, the capture element 330 includes a third capture layer including a non-conductive material. In some examples, the third capture layer can be used to insulate the capture coil 332 from the handle 318 of the device 310. The third capture layer, in some examples, is an outermost layer of the capture element 330. In some examples, the third capture layer can include one or more of a polyether ether ketone (PEEK) material, a polytetrafluoroethylene (PTFE) material, a polyolefin material, or the like. The capture coil 332, in some examples, can be disposed between the second capture layer and third capture layer. In other examples, the capture coil 332 and the first, second, and third layers of the capture element 330 can be differently disposed or otherwise arranged, provided the capture element 330 can function to wirelessly capture the field created by the source coil 382, 382' of the source element.

In some examples, the elongate shaft 314 includes a lumen therethrough similar to the lumen 115 described above with respect to the device 110. The lumen, in various examples, can be used to run various components, conduits, or the like. For instance, in some examples, one or more wires (electrical, fiber optic, data, etc.) can extend through the lumen from the control circuitry 339 to the component. In other examples, one or more conduits can extend within the lumen in order to transport fluids (such as various gases, liquids, and/or other substances) to and/or from a distal end of the elongate shaft 314. In further examples, depending upon the component used with the device 310, various mechanical components can extend within the lumen, such as, but not limited to, a rotational and/or translational shaft, a linkage, one or more pullwires, or the like. In still further examples, wires (electrical, fiber optic, data, etc.) for one or more of various other components can be run within the lumen of the elongate shaft 314, such as, but not limited to, one or more sensors, one or more cameras, one or more lights, one or more lasers, or a combination thereof. In some examples, it should be understood that a combination of two or more of the above-listed examples of wires, conduits, components, etc. can be included within the lumen of the elongate shaft 314, depending upon the application for the device 310.

Figure 4A:
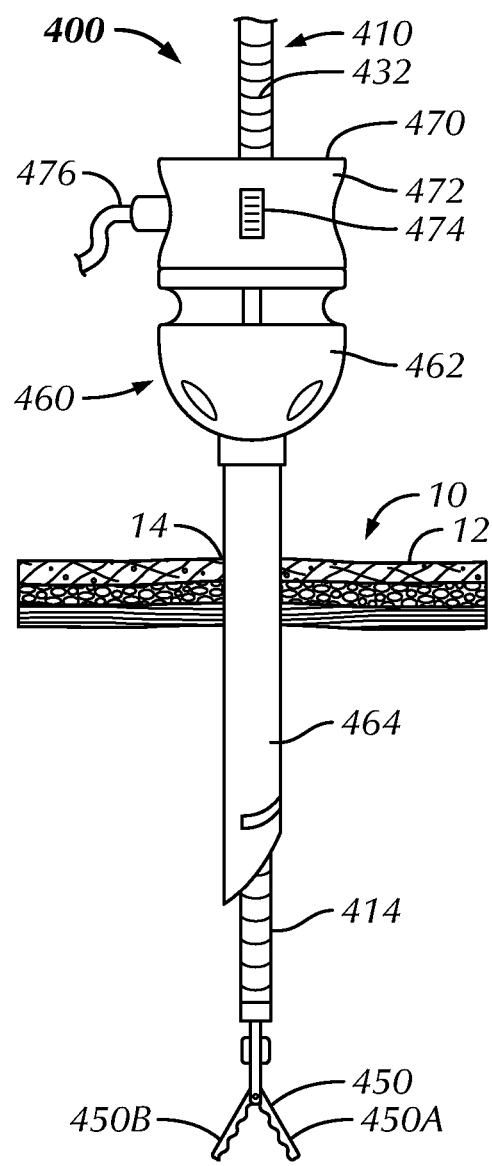
FIG. 4A is a side view of a system for wireless power transfer in accordance with at least one example of the invention.
Figure 4B:
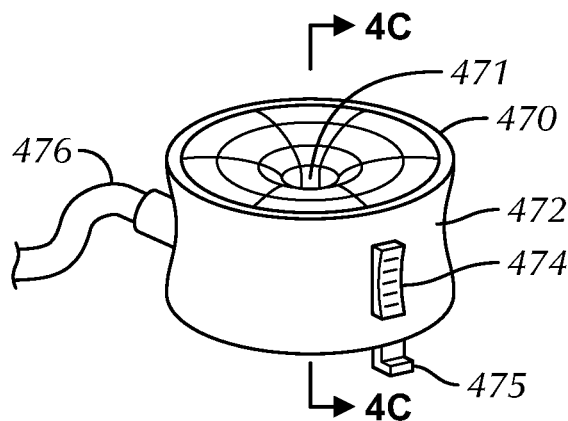
FIG. 4B is a perspective view of a source of the system of FIG. 4A.
Figure 4C:
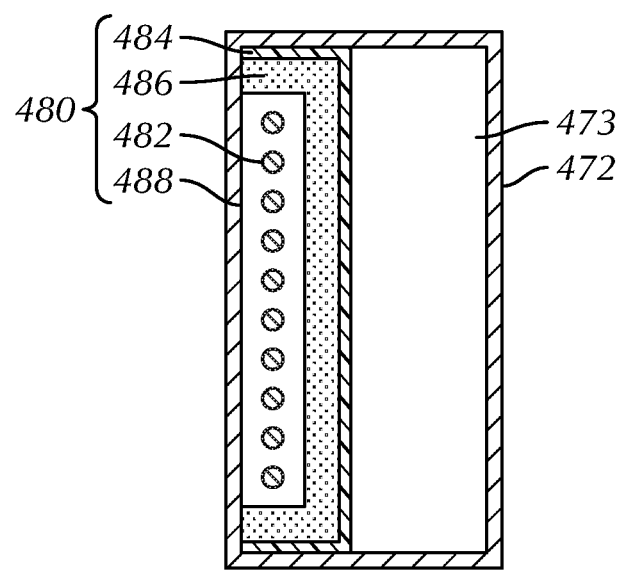
FIG. 4C is a cross-sectional view of the source of FIG. 4B taken along line 4C-4C.

Referring now to FIGS. 4A-4C, in some examples, a system 400 for wirelessly transmitting power using resonant magnetic field power transfer includes a device 410 including at least one component 450 to be wirelessly powered and an access device 460 including a source coil 482 associated with the access device 460 for providing power to be transferred to the device 410. As shown in FIG. 4A, in some examples, the component 450 can include a laparoscopic gripper 450 including jaws 450A, 450B to be powered. In other examples, the component to be powered can include other surgical and/or dental components including, but not limited to those components described and/or listed herein.

In some examples, the device 410 is similar to the device 110 described above. In some examples, the device 410 includes an elongate shaft 414 including a capture coil 432 of a capture element (for instance, similar to the capture element 130 described above) associated with the elongate shaft 414. In some examples, the capture coil 432 is disposed within the shaft 414.

In some examples, the system 400 includes an access device 460 to facilitate access to a location within a patient 10. In some examples, the access device 460 can include a cannula or a port. In some examples, the access device 460 can be inserted through tissue 12 of the patient in order to access the location within the patient 10. In this way, the access device 460 disposed within the patient 10 forms a surgical access point. In some examples, the access device 460 can be inserted through an incision 14 within the tissue 12 of the patient 10. Once the access device 460 is in position within the patient 10, in some examples, various devices including the device 410 can be interchangeably inserted within the access device 460 in order to access the location within the patient 10. In various examples, the location can include a location for a surgical procedure, to perform a measurement, to take one or more images, to illuminate, and/or a combination thereof.

The access device 460, in some examples, includes a handle 462 at a proximal end and a hollow shaft or cannula 464 extending distally from the handle 462. In some examples, the access device 460 includes a passage therethrough to allow access to the location within the patient, for instance, to insert and/or remove various devices (such as the device 410).

In some examples, a source element 480 is associated with the access device 460, the source element 480 including, among other things, the source coil 482. In some examples, the source coil 482 includes a conductive material having a resistivity lower than 12×10$^{-8}$ ohm-meters. In some examples, the source coil 482 can include one or more of copper, aluminum, or the like. In some examples, with insertion of the elongate shaft 414 into the access device 460, the capture coil 432 is placed proximate the source coil 482 to allow power to be wirelessly transmitted from the source coil 482 to the capture coil 432.

In some examples, as seen in FIGS. 4A-4C, the source coil 482 can be disposed within an attachment 470 removably engageable with the access device 460. In some examples, the attachment 470 is removably engageable with a proximal end of the handle 462 of the access device 460. In some examples, the attachment 470 includes a switch 474 or other control to selectively engage and/or disengage the attachment 470 with the access device 460. In further examples, actuation of the switch 474 moves a catch arm 475 between an engaged position and a disengaged position, wherein the catch arm 475 in the engaged position can interact with a complementary recess or other portion of the handle 462 of the access device 460 to attach the attachment 470 to the access device 460. In other examples, the attachment 470 can be configured to be removably engageable with the access device 460 in other ways and/or with other portions of the access device 460. For instance, in some examples, the attachment 470 can be threadably coupled to the access device 460. In other examples, the attachment 470 and the access device 460 can include a snap-on configuration to removably engage the attachment 470 and the access device 460. In still other examples, other engagement configurations of the access device 460 and the attachment 470 are contemplated.

The attachment 470, in some examples, includes a housing 472 including an opening 471 therethrough to allow passage of the device 410 and/or other devices through the attachment 470 and the access device 460 during a procedure. With the elongate shaft 414 of the device 410 inserted through the opening 470 of the attachment 460, in some examples, the capture coil 432 is placed proximate the source coil 482 to allow power to be wirelessly transmitted from the source coil 482 to the capture coil 432. In some examples, the attachment 470 includes a cord 476 to connect to a power source, such as, but not limited to a power outlet, in order to provide power to the source coil 482 to allow the source coil 482 to produce the field for wireless power transfer to the capture coil 432. In some examples, the cord 476 can be configured to connect to a console (described in more detail below), which, in addition to providing power to the source coil 482, can include one or more of various electronic components or modules to control the source coil 482.

In some examples, the source element 480 is associated with the attachment 470. In further examples, the source element 480 is disposed within the housing 472 of the attachment 470. In some examples, the source element 480 is disposed around and proximate the opening 471 of the attachment 470, for instance, to be relatively close to the capture coil 432 with the elongate shaft 414 of the device 410 disposed within the opening 471. In some examples, the source element 480 includes various layers in addition to the source coil 482. For instance, in some examples, the source element 480 includes a first source layer 484 including a material having a skin depth that is less than a thickness of the first source layer 484. In some examples, the first source layer 484 is a material with a relatively high conductivity. The first source layer 484, in some examples, is an outermost layer of the source element 480. In some examples, the first source layer 484 wraps partially around three sides of the source element 480. In some examples, the first source layer 484 can include one or more of copper, aluminum, or the like. In some examples, the source element 480 includes a second source layer 486 including a material having a relative permeability greater than 80 at a particular frequency or frequency range. In some examples, the second source layer 486 includes a material having a relative permeability greater than 80 at a resonant frequency for the system 400. The second source layer 486, in some examples, abuts and is disposed inwardly from the first source layer 484 of the source element 480. In some examples, the second source layer 486 wraps partially around three sides of the source element 480. In some examples, the second source layer 486 can include ferrite. In further examples, the second source layer 486 can include FJ7 ferrite. In some examples, the source element 480 includes a third source layer 488 including a non-conductive material. In some examples, the third source layer 488 can be used as to insulate the source coil 482 from the housing 472 of the attachment 470 and/or the exterior of the housing 472. The third source layer 488, in some examples, is an innermost layer of the source element 480. In some examples, the third source layer 488 is disposed within the housing 472 around and proximate the opening 471 of the attachment 470. In some examples, the housing 472 can provide the third source layer 488, provided the housing 472 is formed from a non-conductive material. In some examples, the third source layer 488 can include one or more of a polyether ether ketone (PEEK) material, a polytetrafluoroethylene (PTFE) material, a polyolefin material, or the like. The source coil 482, in some examples, can be disposed between the second source layer 486 and third source layer 488. In other examples, the source coil 482 and the first, second, and third layers 484, 486, 488 of the source element 480 can be differently disposed or otherwise arranged, provided the source element 480 can function to produce a field which can be wirelessly captured by the capture coil 432 of the capture element.

In some examples, the attachment 470 includes a space 473 within the housing 472. The space 473, in various examples, can be used to house one or more of various electronic components, wires, or the like. In some examples, one or more wires (electrical, fiber optic, data, etc.) can extend within the space 473 between the cord 476 and the source element 480. In some examples, one or more electrical wires connect between the cord 476 and the source coil 482 to power the source coil 482. In some examples, one or more electronic components (for instance, as described in more detail below) can be disposed within the space 473, for instance, for controlling the source coil 482.

Figure 4D:
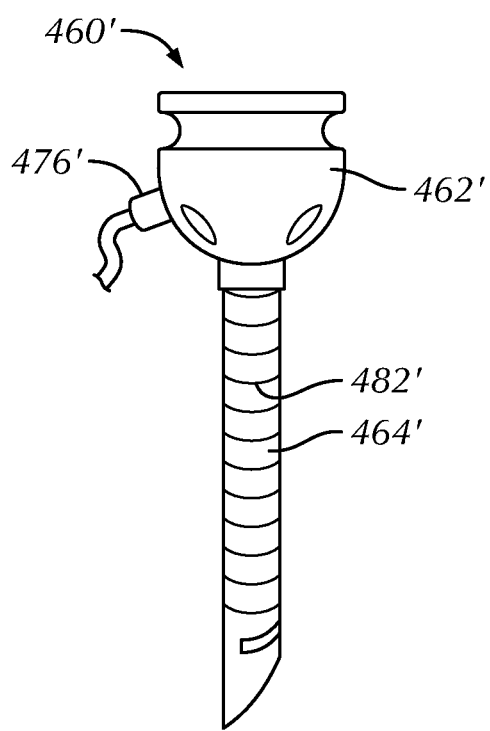
FIG. 4D is a side view of a system for wireless power transfer in accordance with at least one example of the invention.
Figure 4E:
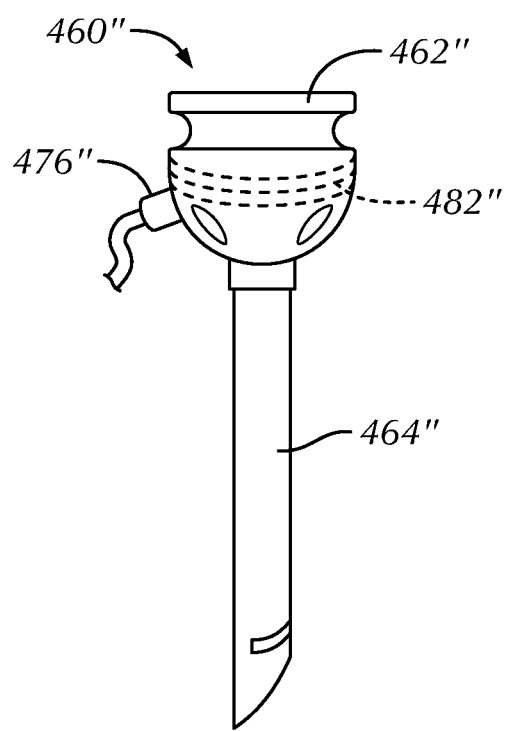
FIG. 4E is a side view of a system for wireless power transfer in accordance with at least one example of the invention.

Referring to FIGS. 4D and 4E, an access device 460', 460" can include a source coil 482', 482" disposed within a portion of the access device 460', 460", either instead of or in addition to the configuration described above and shown in FIGS. 4A-4C with the attachment 470 including the source coil 482, the attachment 470 being removably engageable with the access device 460. In some examples, the access device 460', 460" includes a handle 462', 462" disposed at a proximal end of a cannula 464', 464". In some examples, the access device 460', 460" includes a cord 476', 476" to connect to a power source, such as, but not limited to a power outlet, in order to provide power to the source coil 482', 482" to allow the source coil 482', 482" to produce the field for wireless power transfer to a capture coil. In some examples, the cord 476', 476" can be configured to connect to a console (described in more detail below), which, in addition to providing power to the source coil 482', 482", can include one or more of various electronic components or modules to control the source coil 482', 482".

In some examples, as shown in FIG. 4D, the access device 460' can include the source coil 482' associated with the cannula 464' of the access device 460'. For instance, in some examples, the source coil 482' can be disposed within a wall of the cannula 464'. In this way, with a device similar to device 410 of FIGS. 4A-4C disposed within the cannula 464', the capture coil within an elongate shaft of the device is placed proximate the source coil 482' to allow power to be wirelessly transmitted from the source coil 482' to the capture coil.

In other examples, as shown in FIG. 4E, the access device 460" can include the source coil 482" associated with the handle 462" of the access device 460". For instance, in some examples, the source coil 482" can be disposed within a wall of the handle 462". In this way, with a device similar to device 410 of FIGS. 4A-4C disposed within the handle 462", the capture coil within an elongate shaft of the device is placed proximate the source coil 482" to allow power to be wirelessly transmitted from the source coil 482" to the capture coil.

Figure 5:
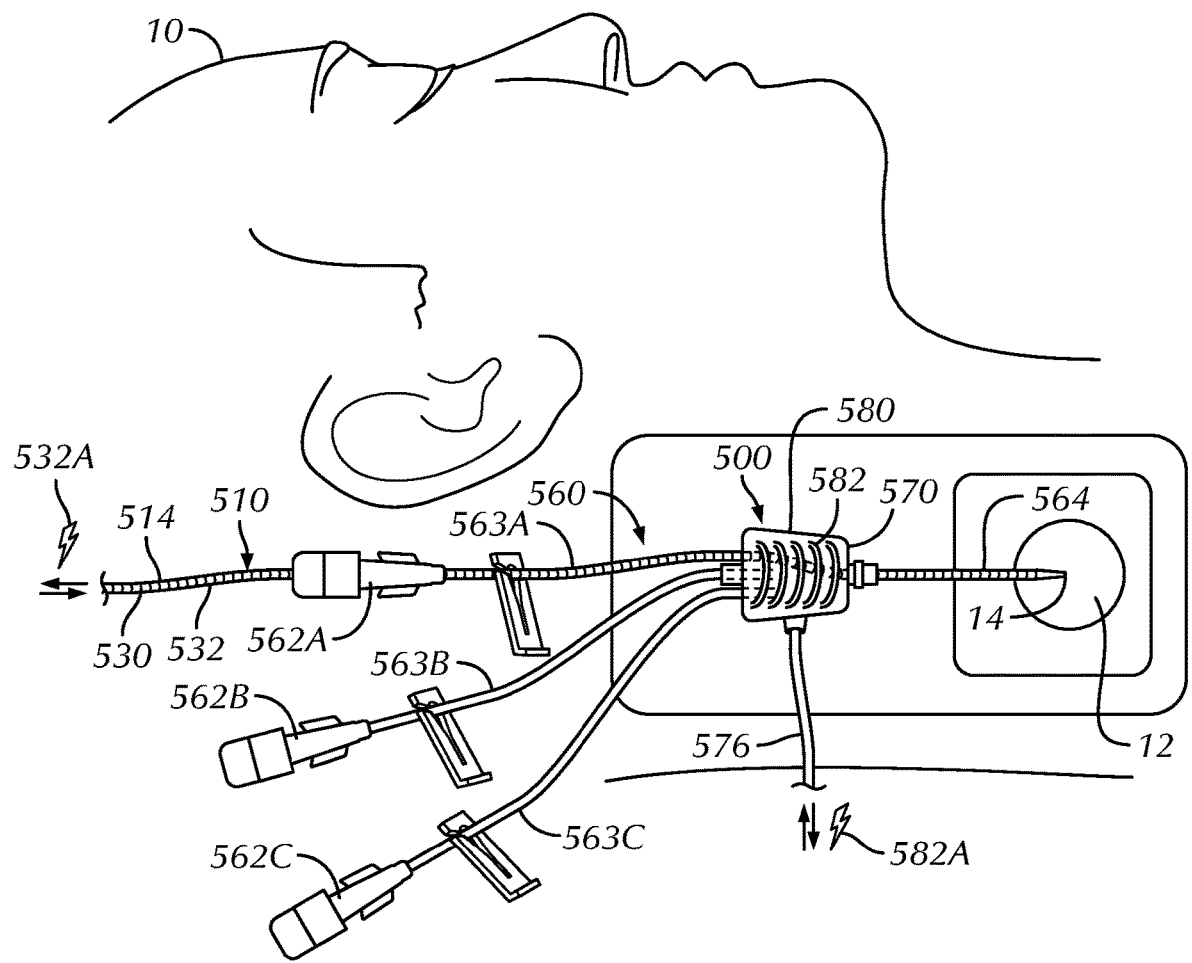
FIG. 5 is a perspective view of a system for wireless power transfer in accordance with at least one example of the invention.

Referring to FIG. 5, in some examples, a system 500 includes an introducer port 560 for wirelessly transmitting power using resonant magnetic field power transfer. In some examples, the introducer port 560 can be used for percutaneous/trans-arterial access. In some examples, the system 500 includes a device 510 including at least one component to be wirelessly powered. In various examples, the device 510 can include a catheter, a guidewire, or the like. In various examples, the component can include one or more of the following: a sensor, an imaging component, an illumination component, an ablation component, or the like. In other examples, the component to be powered can include any of various types of components described herein. As such, in various examples, the device 510 can include any of various types of devices, including, but not limited to, a medical device, for instance, for use in one of the above-listed procedures. In some examples, the introducer port 560 can be inserted into a puncture or an incision 14 in tissue 12 of a patient 10. In some examples, the device 510 can include control circuitry which is wirelessly powered and then, in turn, controls the component. In some examples, the device 510 includes an elongate shaft 514 and a capture element 530 including a capture coil 532.

In some examples, the system 500 includes a source element 580 for wirelessly supplying power to the device 510. In some examples, the source element 580 is substantially similar to the source element 480 described. In further examples, the source element 580 includes various layers similar to those described above with respect to the source element 480. In some examples, the source element 580 is associated with a source unit 570 configured to wirelessly transfer power to the capture coil 532 of the device 510. In the example of FIG. 5, the source unit 570 includes a three-way convergence for the introducer port 560. For instance, in some examples, the introducer port 560 includes three branches 563A, 563B, 563C extending from a proximal side of the source unit 570. While described herein as having three branches 563A, 563B, 563C, in other examples, the introducer port can include a single port (like a sheath or single lumen introducer), two branches, or more than three branches, depending upon the procedure. The three-branch introducer port 560 described herein is merely exemplary and should not be so limited. In some examples, each of the branches 563A, 563B, 563C includes an access port 562A, 562B, 562C configured for insertion of one or more devices (including, for instance, device 510), connection to positive or negative pressure, connection to a fluid, or the like. Extending from a distal end of the source unit 570, in some examples, is a single cannula 564 configured for insertion within the patient 10, for instance through the puncture or incision 14 in the tissue 12. In this way, a device (including, for instance, device 510) can be inserted into any of the access ports 562A, 562B, 562C in order to push through the source unit 570 and the cannula 564 for access to a location within the patient 10, for instance, in order to perform a procedure.

In some examples, the source element 580 is disposed within the source unit 570. In some examples, the source element 580 includes a source coil 582 disposed proximate a passageway within and through the source unit 570. In some examples, the source coil 582 is disposed around the passageway. The passageway can be sized to allow the elongate shaft 514 of the device 510 to fit therein. In some examples, the source coil 582 is located proximate the passageway, wherein, with insertion of the elongate shaft 514 within the passageway of the source unit 570, the capture coil 532 is disposed sufficiently proximate the source coil 582 to allow power to be wirelessly transmitted from the source coil 582 to the capture coil 532 to power the at least one component of the device 510.

In some examples, the source coil 582 receives power 582A, for instance, from being plugged into an electrical outlet or otherwise supplied with power. In some examples, the source unit 570 includes a cord 576 to connect to a power source, such as, but not limited to a power outlet, in order to provide power to the source coil 582 to allow the source coil 582 to produce a field for wireless power transfer to the capture coil 532. In some examples, the cord 576 can be configured to connect to a console (described in more detail below), which, in addition to providing power to the source coil 582, can include one or more of various electronic components or modules to control the source coil 582. With the elongate shaft 514 (and, in turn, the capture coil 532) of the device 510 disposed within or otherwise proximate the source coil 582, in some examples, the power 582A can be wirelessly transferred from the source coil 582 to the capture coil 532 to supply power 532A to the device 510. In some examples, the capture coil 532 is electrically coupled directly to the component, such that the power 532A is supplied directly to the component. In other examples, the capture coil 532 is electrically coupled to control circuitry, such that the power 532A is supplied to the control circuitry to power and control the component. In some examples, the control circuitry is disposed at a proximal end of the device 510.

In some examples, with the elongate shaft 514 disposed at least partially within the source unit 570, the capture coil 532 is disposed proximate the source coil 582 to allow the wireless transfer of power from the source coil 582 to the capture coil 532. In some examples, with the capture coil 532 extending along a length of the elongate shaft 514, the capture coil 532 can be disposed within and/or proximate the source coil 582 at various positions of the device 510 with respect to the patient 10 and/or the introducer port 560 and the source unit 570 to ensure adequate power transfer from the source coil 582 to the capture coil 532, for instance, during a procedure. That is, as long as a portion of the capture coil 532 is disposed proximate the source coil 582, power can be transferred to the device 510 to power the component of the device 510. In this way, power can be transferred to the device 510 at various locations of the device 510 relative to the source unit 570. Although shown and described as having the device 510 inserted within the access port 562A and running within the branch 563A, in some examples, it should be understood that a device (including, for instance, device 510) can be inserted within any of the other ports 562B, 562C to pass through the respective branches 563B, 563C to the source unit 570 to allow for the wireless transfer of power to devices within the other ports 562B, 562C, provided the device includes a capture coil, such as the capture coil 532 of the device 510, for instance.

Figure 6A:
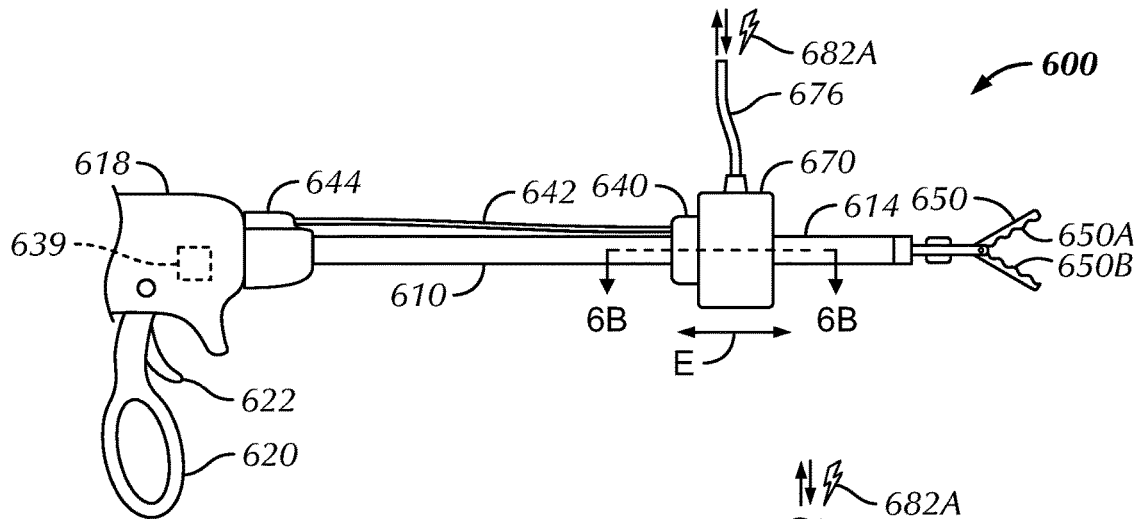
FIG. 6A is a side view of a system for wireless power transfer in accordance with at least one example of the invention.
Figure 6B:
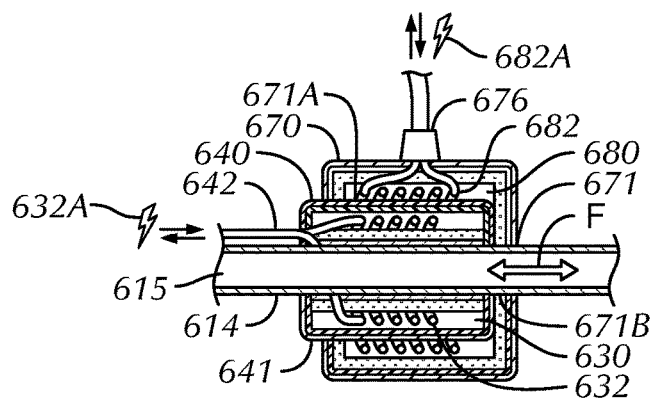
FIG. 6B is a cross-sectional view of a source and a capture for the system of FIG. 6A taken along line 6A-6A.
Figure 6C:
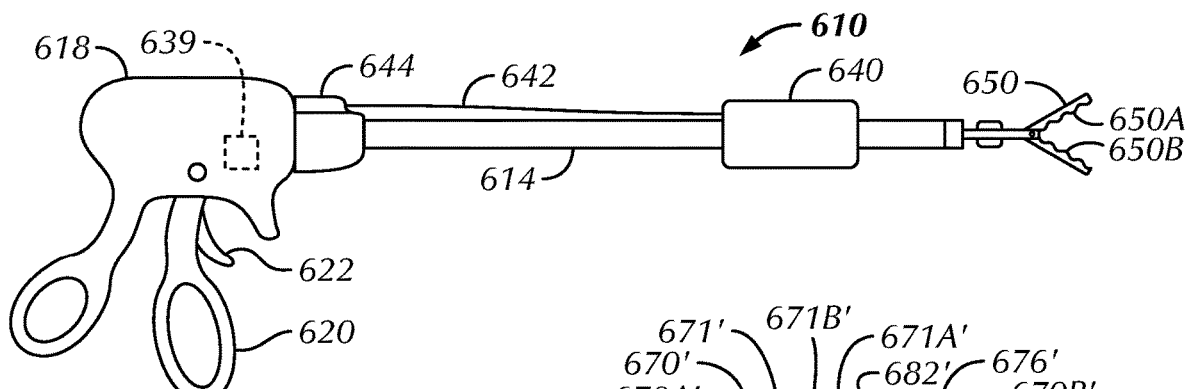
FIG. 6C is a side view of a wirelessly powered device of the system of FIG. 6A.

Referring now to FIGS. 6A-6C, in some examples, a system 600 for wirelessly transmitting power using resonant magnetic field power transfer can be seen. In some examples, the system 600 includes a device 610 including at least one component 650 to be wirelessly powered. In some examples, the system 600 can be used in a procedure without an access device. That is, in some examples, it is contemplated that the system 600 can be used to power the device 610 when inserted into an incision 14, orifice, or other access point of a patient 10 without the use of an access device, such as an introducer, a cannula, a dilator, a port, or the like. In some examples, the component 650 to be powered can include a gripper 650 including jaws 650A, 650B to be powered. In other examples, the component to be powered can include any of various types of components described herein. As such, in various examples, the device 610 can include any of various types of devices, including, but not limited to, a medical device and/or a dental device, for instance, for use in one of the above-listed procedures. In some examples, the device 610 can include control circuitry 639 which is wirelessly powered and then, in turn, controls the component 650. The device 610, in some examples, is substantially similar to the device 210 described above. In some examples, the device 610 includes an elongate shaft 614 and a capture element 630 including a capture coil 632.

In some examples, the system 600 includes a source element 680 for wirelessly supplying power to the device 610. In some examples, the source element 680 is substantially similar to the source element 480 described above. In further examples, the source element 680 includes various layers similar to those described above with respect to the source element 480. In some examples, the source element 680 is associated with a source unit 670 configured to wirelessly transfer power to the capture coil 632 of the device 610. In some examples, the source element 680 is disposed within the source unit 670. In some examples, the source element 680 includes a source coil 682 disposed proximate an opening 671 of the source element 680 and/or the source unit 670. In some examples, the source coil 682 is disposed around the opening 671. The opening 671 can be sized to allow the elongate shaft 614 of the device 610 to fit therein. In some examples, the source coil 682 is located proximate a surgical access point, wherein, with insertion of the elongate shaft 614 within the opening 671 of the source element 680, the capture coil 632 is disposed sufficiently proximate the source coil 682 to allow power to be wirelessly transmitted from the source coil 682 to the capture coil 632 to power the at least one component 650 of the device 610.

In some examples, the capture element 630 of the device 610 can be disposed within a slider 640 translatable (arrow E) along the elongate shaft 614 of the device 610, such that having the slider 640 disposed proximate the source coil 682 allows for the wireless transfer of power from the source coil 682 to the capture coil 632. In some examples, the elongate shaft 614 extends outwardly from the handle 618, with the slider 640 sliding along the elongate shaft 614. In some examples, a tether 642 extends between a retractor 644 and the slider 640. In some examples, the tether 642 includes a wire electrically coupling the capture coil 632 within the slider 640 back to a handle 618 to then be electrically coupled to control circuitry 639 and/or the component 650. In some examples, the retractor 644 allows for extension of the tether 642, for instance, when the slider 640 is moved distally along the elongate shaft 614, and for retraction of the tether 642, for instance, when the slider 640 is moved proximally along the elongate shaft 614. In this way, the tether 642 can be maintained relatively taut and/or close to the shaft 614 and/or handle 618 of the device 610, thereby decreasing the chances that the tether 642 gets snagged or otherwise caught up by an object or person during use. While the present examples of the device 610 are described as including the slider 640, it should be understood that the device 610 could include the capture coil 632 in a different portion of the device 610, including, but not limited to, the elongate shaft 614 (similar to the device 110 described above) and/or the handle 618 (similar to the device 310 described above). It should further be understood that the source unit 640 can be differently configured than is described herein to accommodate the capture coil 632 disposed in different portions of the device 610.

When used with the slider 640 of the device 610, in some examples, the opening 671 of the source unit 670 can include a wide portion 671A and a narrow portion 671B. In some examples, the wide portion 671A is sized and shaped to accommodate the slider 640 at least partially within the wide portion 671A of the source unit 670. In some examples, the narrow portion 671B is sized and shaped to accommodate the elongate shaft 614 of the device 610 therein. Such a configuration allows for the slider 640 to nest at least partially within the source unit 670, for instance when it is desired to power the device 610. In some examples, the source unit 670 can be selectively engageable with the slider 640, for instance with a snap connection, a clasp, a threaded connection, or the like. In other examples, the slider 640 loosely fits within the source unit 670. With such a configuration, the physician or other user can retain the slider 640 within the source unit 670 during use of the device 610 using a hand or the like.

In some examples, with the capture element 630 slidable along a length of the shaft 614, the shaft 614 of the device 610 can be moved along arrow F with respect to the source coil 682 while still maintaining the capture coil 632 proximate the source coil 682, thereby allowing for power transfer from the source coil 682 to the capture coil 632 at a range of locations of the elongate shaft 614 with respect to the source coil 682. That is, in some examples, the device 610 and, in turn, the elongate shaft 614 can be moved along arrow F without interrupting power transfer from the source coil 682 to the capture coil 632.

In some examples, the source coil 682 receives power 682A, for instance, from being plugged into an electrical outlet or otherwise supplied with power. In some examples, the source unit 670 includes a cord 676 to connect to a power source, such as, but not limited to a power outlet, in order to provide power to the source coil 682 to allow the source coil 682 to produce a field for wireless power transfer to the capture coil 632. In some examples, the cord 676 can be configured to connect to a console (described in more detail below), which, in addition to providing power to the source coil 682, can include one or more of various electronic components or modules to control the source coil 682. With the slider 640 of the device 610 disposed within or otherwise proximate the source coil 682, in some examples, the power 682A can be wirelessly transferred from the source coil 682 to the capture coil 632 to supply power 632A to the device 610. In some examples, the capture coil 632 is electrically coupled directly to the component 650, such that the power 632A is supplied directly to the component 650. In other examples, the capture coil 632 is electrically coupled to control circuitry 639, such that the power 632A is supplied to the control circuitry 639 to power and control the component 650. In some examples, the control circuitry 639 is disposed within the handle 618 of the device 610.

In some examples, the physician or other user can control the component 650 using a control 620. The control 620, in various examples, can be disposed on or extending from the handle 618. In some examples, the device 610 includes more than one control 620, 622 to control different aspects of the component 650. For instance, the device 610 can include a first control 620 to operate (for instance, close and/or open) the jaws 650A, 650B of a gripper 650. In some examples, the device 610 can further or alternatively include a second control 622 to operate (for instance, turn on and/or turn off) a cauterizer, a stapler, suction, saline, or the like.

In some examples, the capture element 630 is associated with the slider 640 of the device 610. In further examples, the capture element 630 is disposed within the slider 640 of the device 610. In some examples, the capture element 630 is substantially similar to the capture element 130 described above except that the capture element 630 is associated with the slider 640. In further examples, the capture element 630 includes various layers similar to those described above with respect to the capture element 130. In some examples, the capture element 630 is disposed proximate an exterior surface of the slider 640. In some examples, the capture element 630 is disposed within a housing 641 of the slider 640. In addition to the capture element 630, the slider 640 can also include space within the housing 641, for instance, to house components in addition to the capture element 630, such as, but not limited to electronic modules or other components, wiring, or the like.

Referring specifically to FIG. 6B, in some examples, with the slider 640 disposed at least partially within the opening 671, the capture coil 632 is disposed proximate the source coil 682 to allow the wireless transfer of power from the source coil 682 to the capture coil 632. In some examples, with the slider 640 disposed at least partially within the source unit 670, the capture coil 632 is disposed within and proximate the source coil 682 to ensure adequate power transfer from the source coil 682 to the capture coil 632. By placing the capture coil 632, in some examples, within the slider 640, the elongate shaft 614 of the device 610 can be moved along arrow F with respect to the slider 640, for instance to perform at least a part of a procedure using the device 610, while still maintaining the source coil 682 proximate to the capture coil 632. In this way, power can be transferred to the device 610 at various locations of the device 610 relative to the source unit 670.

Figure 6D:
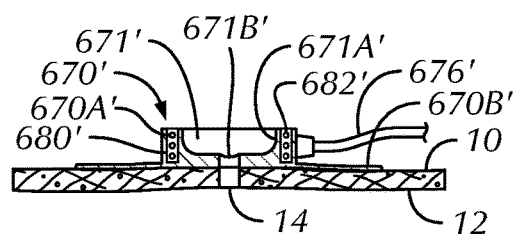
FIG. 6D is a cross-sectional view of a source for use with the wirelessly powered device of FIG. 6C.

Referring to FIGS. 6C and 6D, in some examples, a source element 680' is associated with an attachment member 670' configured to attach directly to a patient 10. In some examples, the source element 680' is substantially similar to the source element 480 described above except that the source element 680' is associated with the attachment member 670'. In further examples, the source element 680' includes various layers similar to those described above with respect to the source element 480.

In some examples, the attachment member 670' can be attached to tissue 12 of the patient 10. For instance, in some examples, the attachment member 670' can include a patch configured to be adhered to the patient 10, using glue, an adhesive, tape, wrap, and/or another fastening technique. In some examples, the attachment member 670' includes the source coil 682' disposed within the attachment member 670'. In some examples, the surgical access point is an incision 14 with the attachment member 670' being configured to be placed at the incision 14 so that insertion of the elongate shaft 614 of the device 610 into the incision 14 places the capture coil 632 proximate the source coil 682' to allow power to be wirelessly transmitted from the source coil 682' to the capture coil 632. In the example of FIGS. 6C and 6D, with the capture coil 632 disposed within the slider 640, the attachment member 670' can be configured to accept at least a portion of the slider 640 within the attachment member 670'. To that end, in some examples, the attachment member 670' includes an opening 671' including a wide portion 671A' configured to accept at least a portion of the slider 640 therein and a narrow portion 671B' configured to allow the elongate shaft 614 to pass therethrough in order to access the incision 14 and enter the patient 10, for instance, during a procedure. Such a configuration allows for the slider 640 to nest at least partially within the attachment member 670', for instance when it is desired to power the device 610. In some examples, the attachment member 670' can be selectively engageable with the slider 640, for instance with a snap connection, a clasp, a threaded connection, or the like. In other examples, the slider 640 loosely fits within the attachment member 670'. With such a configuration, the physician or other user can retain the slider 640 within the attachment member 670' during use of the device 610 using a hand or the like.

In some examples, the attachment member 670' includes a first portion 670A' and a second portion 670B'. In some examples, the first portion 670A' can be raised with respect to the second portion 670B' to accommodate the source coil 682' therein. In some examples, the second portion 670B' provides a relatively wide base for the attachment member 670', for instance to allow for an increased surface area for adhesive, glue, tape, wrap, or the like to facilitate and/or enhance fastening of the attachment member 670' to the patient 10.

In some examples, the attachment member 670' includes a cord 676' to connect to a power source, such as, but not limited to a power outlet, in order to provide power to the source coil 682' to allow the source coil 682' to produce the field for wireless power transfer to the capture coil 632. In some examples, the cord 676' can be configured to connect to a console (described in more detail below), which, in addition to providing power to the source coil 682', can include one or more of various electronic components or modules to control the source coil 682'.

While the present examples of the device 610 are described as including the slider 640, it should be understood that the device 610 could include the capture coil 632 in a different portion of the device 610, including, but not limited to, the elongate shaft 614 (similar to the device 110 described above) and/or the handle 618 (similar to the device 310 described above).

Figure 7A:
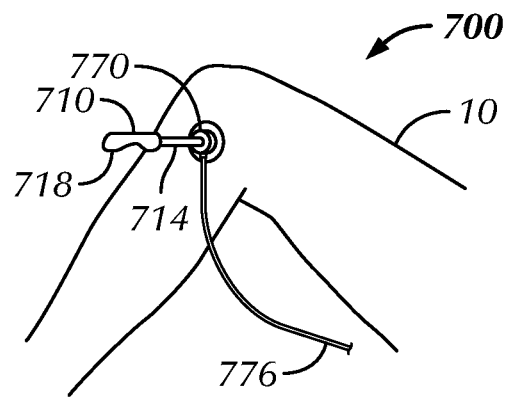
FIG. 7A is a side view of a system for wireless power transfer in accordance with at least one example of the invention.
Figure 7B:
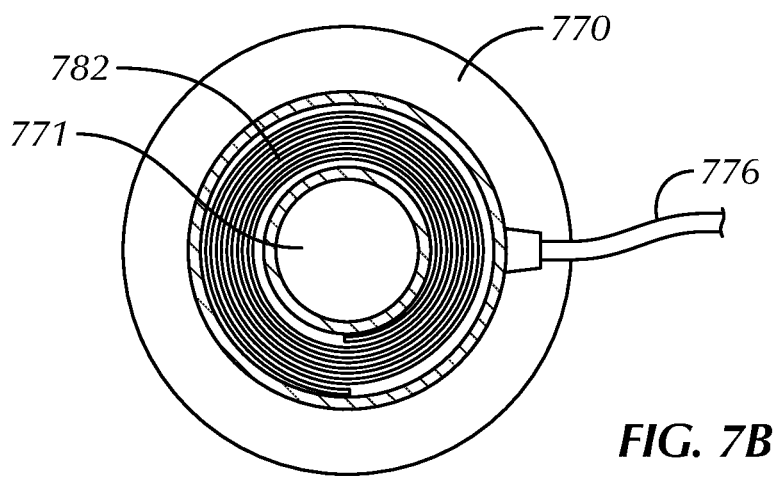
FIG. 7B is a top view of a source of the system of FIG. 7A.
Figure 7C:
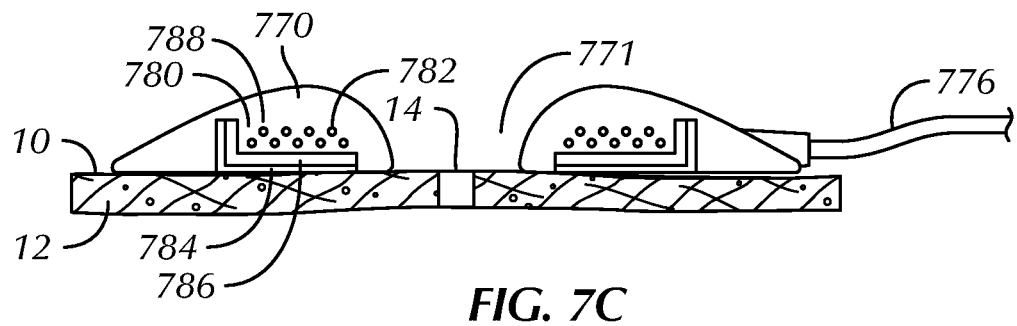
FIG. 7C is a side cross-sectional view of the source of FIG. 7B.

Referring now to FIGS. 7A-7C, in some examples, a system 700 for wirelessly transmitting power using resonant magnetic field power transfer can be seen. In some examples, the system 700 includes a device 710 including at least one component to be wirelessly powered. In some examples, the system 700 can be used in a procedure without an access device. For instance, the example shown in FIG. 7A includes an arthroscopic device 710, such as, but not limited to, a shaver, a burr, an ablation device, a gripper, or the like. In some examples, it is contemplated that the system 700 can be used to power the device 710 when inserted into an incision 14, orifice, or other access point of a patient 10 without the use of an access device, such as an introducer, a cannula, a dilator, a port, or the like. In some examples, the device 710 can include control circuitry (for instance, disposed within a handle 718 of the device 710) which is wirelessly powered and then, in turn, controls the device 710 or a component of the device 710. The device 710, in some examples, is substantially similar to the device 110 described above. In some examples, the device 710 includes an elongate shaft 714 and a capture element including a capture coil (for instance, similar to the capture element 130 and the capture coil 132 described above) associated with the elongate shaft 714. In other examples, however, the capture element and the capture coil can be associated with a slider of the device 710 (similar to the device 210 described above) or disposed within the handle 718 of the device 710 (similar to the device 310 described above).

In some examples, the system 700 includes a source element 780 for wirelessly supplying power to the device 710. In some examples, the source element 780 is substantially similar to the source element 480 described above except that the source element 780 is associated with an attachment member 770. In some examples, the source coil 782 includes a conductive material having a resistivity lower than $12 \times 10^{-8}$ ohm-meters. In some examples, the source coil 782 can include one or more of copper, aluminum, or the like. In some examples, the source element 780 includes various layers similar to those described above with respect to the source element 480. For instance, in some examples, the source element 780 includes a first source layer 784 including a material having a skin depth that is less than a thickness of the first source layer 784. In some examples, the first source layer 784 is a material with a relatively high conductivity. The first source layer 784, in some examples, is a lowermost layer of the source element 780 (as seen in FIG. 7C). In some examples, the first source layer 784 wraps partially around two sides of the source element 780. In some examples, the first source layer 784 can include one or more of copper, aluminum, or the like. In some examples, the source element 780 includes a second source layer 786 including a material having a relative permeability greater than 80 at a particular frequency or frequency range. In some examples, the second source layer 786 includes a material having a relative permeability greater than 80 at a resonant frequency for the system 700. The second source layer 786, in some examples, abuts and is disposed upwardly from the first source layer 784 of the source element 780 (as seen in FIG. 7C). In some examples, the second source layer 786 wraps partially around two sides of the source element 780. In some examples, the second source layer 786 can include ferrite. In further examples, the second source layer 786 can include FJ7 ferrite. In some examples, the source element 780 includes a third source layer 788 including a non-conductive material. In some examples, the third source layer 788 can be used as to insulate the source coil 782 from the attachment member 770 and/or objects outside of the attachment member 770. The third source layer 788, in some examples, is an uppermost layer of the source element 780 (as seen in FIG. 7C). In some examples, the third source layer 688 is disposed within the attachment member 770 around and proximate the opening 771 of the attachment member 770. In some examples, the attachment member 770 provides the third source layer 788, provided the attachment member 770 is formed from a non-conductive material. Additional material can be included within the third source layer 788, for instance, for the purposes of thermal management or electromagnetic interference (EMI) shielding. In some examples, the third source layer 788 can include one or more of a polyether ether ketone (PEEK) material, a polytetrafluoroethylene (PTFE) material, a polyolefin material, or the like. The source coil 782, in some examples, can be disposed between the second source layer 786 and third source layer 788. In other examples, the source coil 782 and the first, second, and third layers 784, 786, 788 of the source element 780 can be differently disposed or otherwise arranged, provided the source element 780 can function to produce a field which can be wirelessly captured by the capture coil 732 of the capture element.

In some examples, the source element 780 is associated with the attachment member 770 configured to wirelessly transfer power to the capture coil of the device 710. In some examples, the source element 780 is disposed within the attachment member 770. In some examples, the source coil 782 is disposed proximate an opening 771 of the source element 780 and/or the attachment member 770. In some examples, the source coil 782 is disposed around the opening 771. The opening 771 can be sized to allow the elongate shaft 714 of the device 710 to fit therein. In some examples, the source coil 782 is located proximate a surgical access point, wherein, with insertion of the elongate shaft 714 within the opening 771 of the source element 780, the capture coil is disposed sufficiently proximate the source coil 782 to allow power to be wirelessly transmitted from the source coil 782 to the capture coil to power the at least one component of the device 710. In some examples, the source coil 782 includes a planar coil, for instance, to maintain a relatively flattened profile of the attachment member 770. In some examples, the attachment member 770 can be a flat disk or membrane with the opening 771 in a center of the disk to allow for access through the incision 14 or placement of a port.

In some examples, the attachment member 770 is configured to attach directly to the patient 10. In some examples, the attachment member 770 can be attached to tissue 12 of the patient 10. For instance, in some examples, the attachment member 770 can include a patch configured to be adhered to the patient 10, using glue, an adhesive, tape, wrap, and/or another fastening technique. In some examples, the attachment member 770 can be fastened or adhered to the a surgical drape. In some examples, the attachment member 770 includes the source coil 782 disposed within the attachment member 770. In some examples, the surgical access point is the incision 14 with the attachment member 770 being configured to be placed at the incision 14 so that insertion of the elongate shaft 714 of the device 710 into the incision 14 places the capture coil proximate the source coil 782 to allow power to be wirelessly transmitted from the source coil 782 to the capture coil.

In some examples, the attachment member 770 includes a relatively wide base, for instance to allow for an increased surface area for adhesive, glue, tape, wrap, or the like to facilitate and/or enhance fastening of the attachment member 770 to the patient 10.

In some examples, the attachment member 770 includes a cord 776 to connect to a power source, such as, but not limited to a power outlet, in order to provide power to the source coil 782 to allow the source coil 782 to produce the field for wireless power transfer to the capture coil. In some examples, the cord 776 can be configured to connect to a console (described in more detail below), which, in addition to providing power to the source coil 782, can include one or more of various electronic components or modules to control the source coil 782.

Figure 8A:
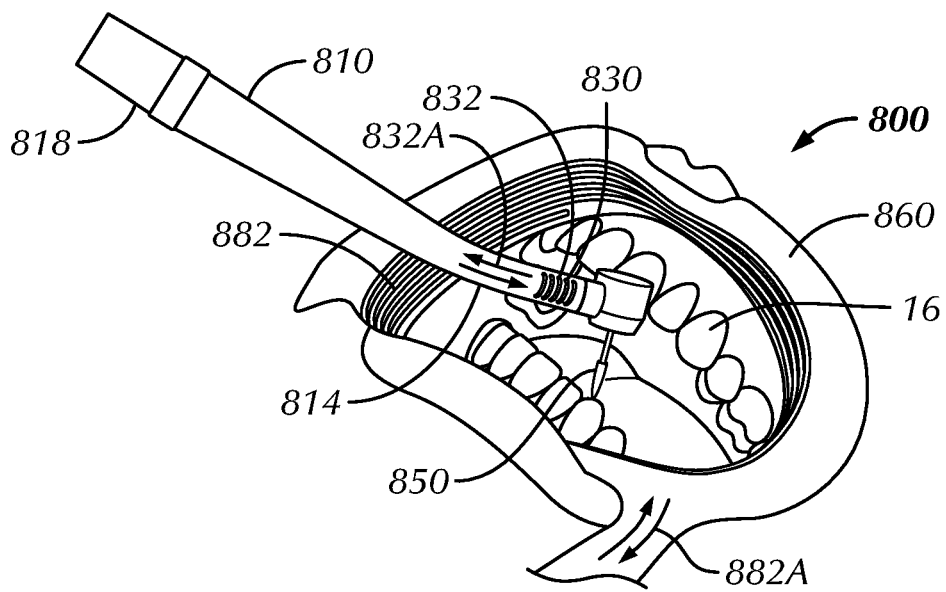
FIG. 8A is a perspective view of a system for wireless power transfer in accordance with at least one example of the invention.
Figure 8B:
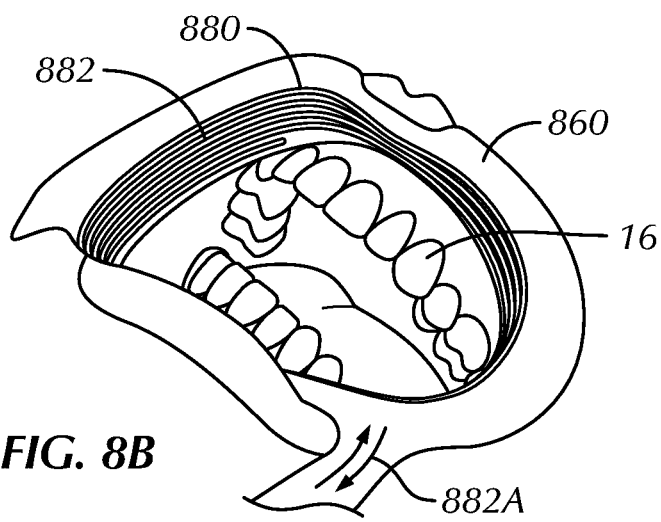
FIG. 8B is a perspective view of a source of the system of FIG. 8A.
Figure 8C:
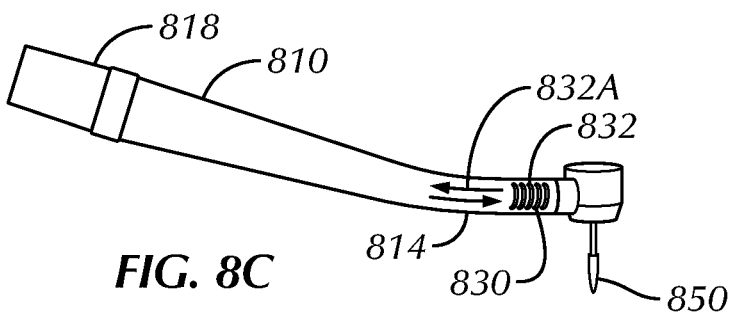
FIG. 8C is a perspective view of a wirelessly powered device of the system of FIG. 8A.
Figure 9:
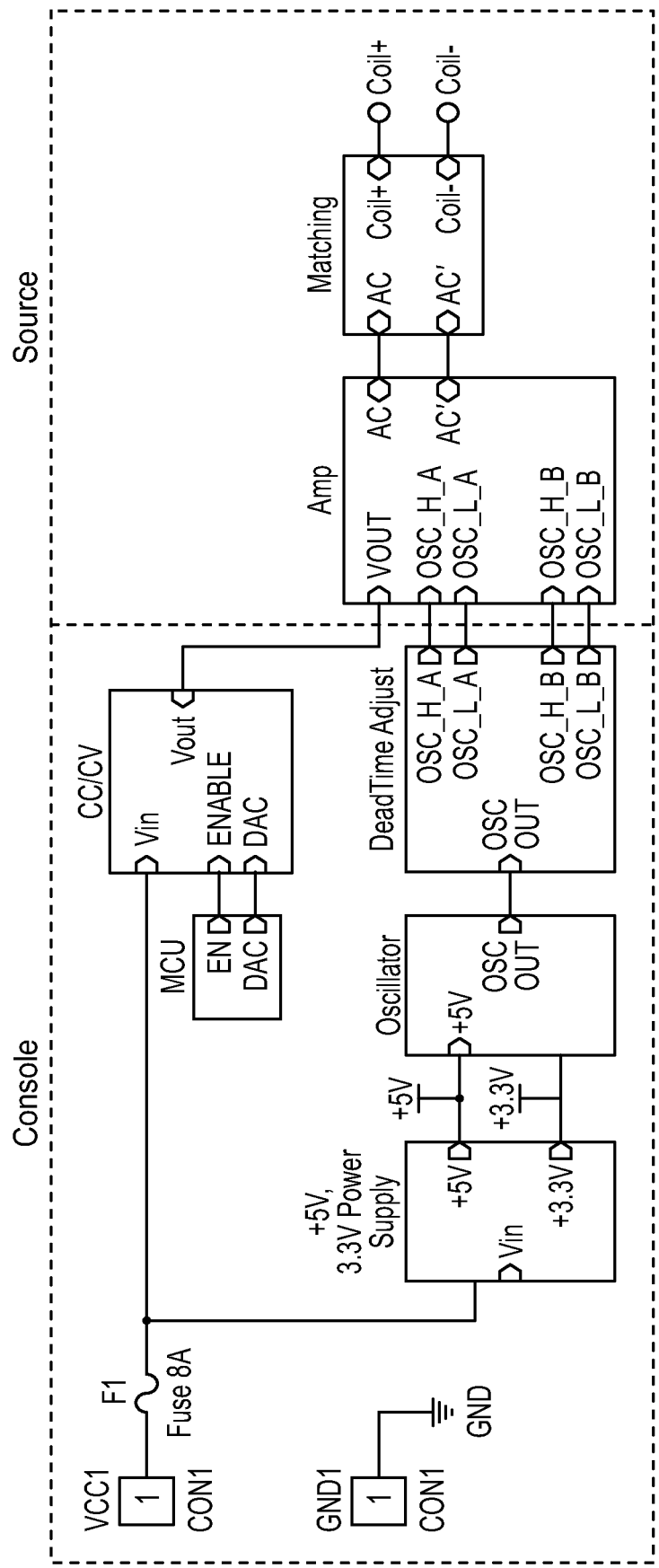
FIG. 9 is a schematic of a system for wireless power transfer in accordance with at least one example of the invention.
Figure 10:
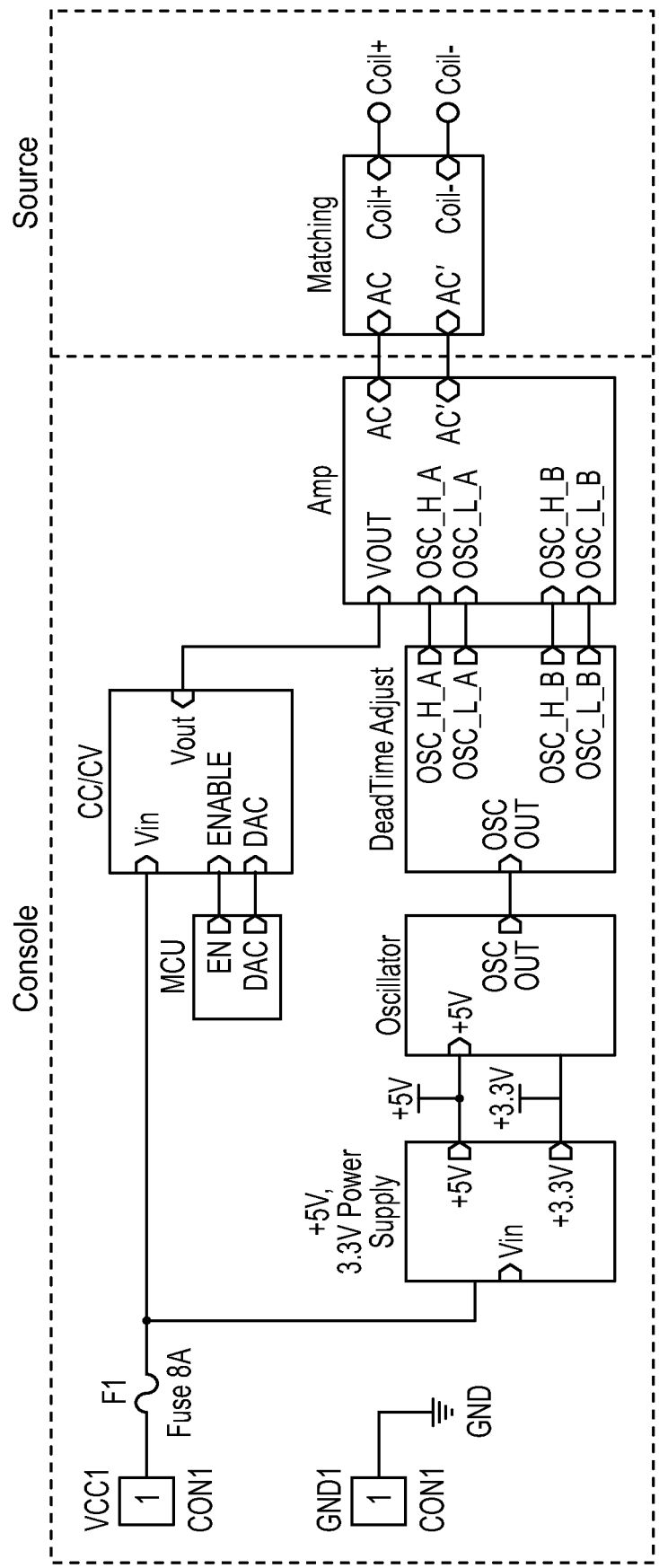
FIG. 10 is a schematic of a system for wireless power transfer in accordance with at least one example of the invention.
Figure 11:
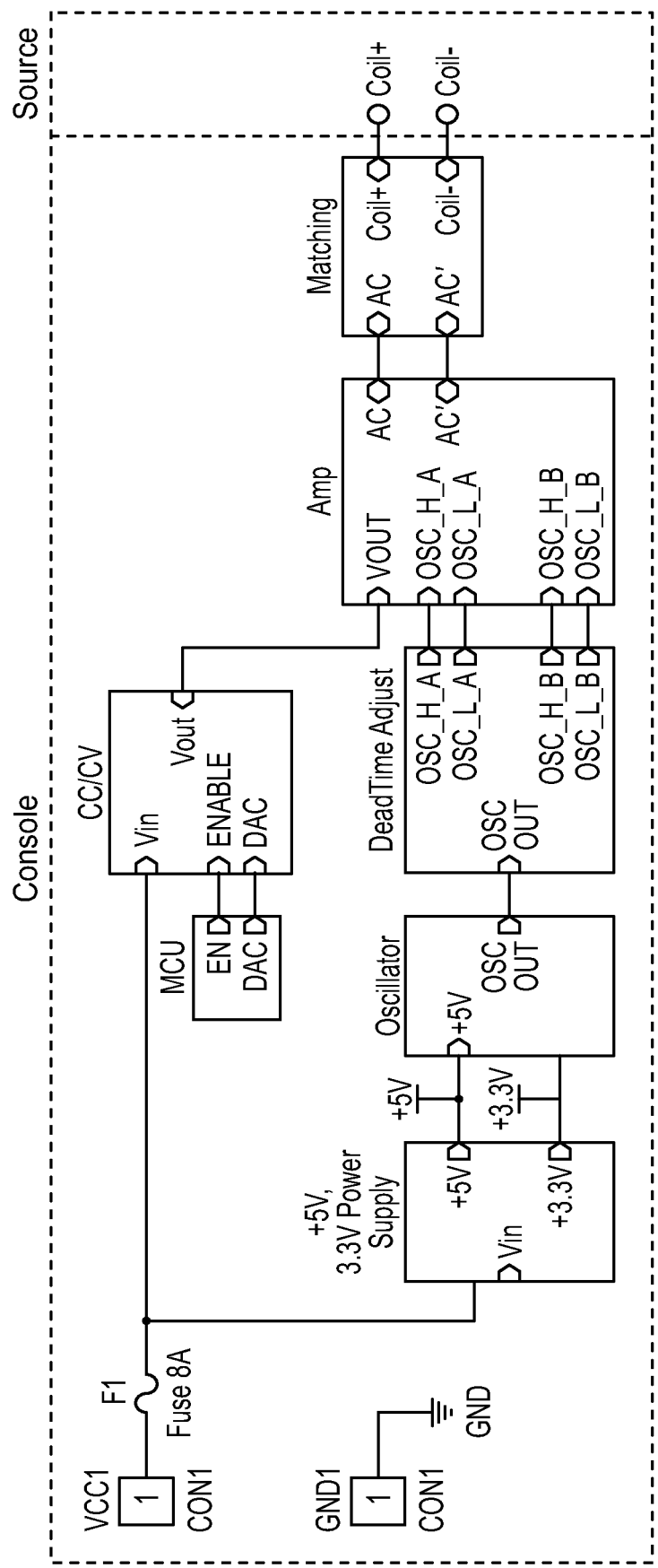
FIG. 11 is a schematic of a system for wireless power transfer in accordance with at least one example of the invention.
Figure 12:
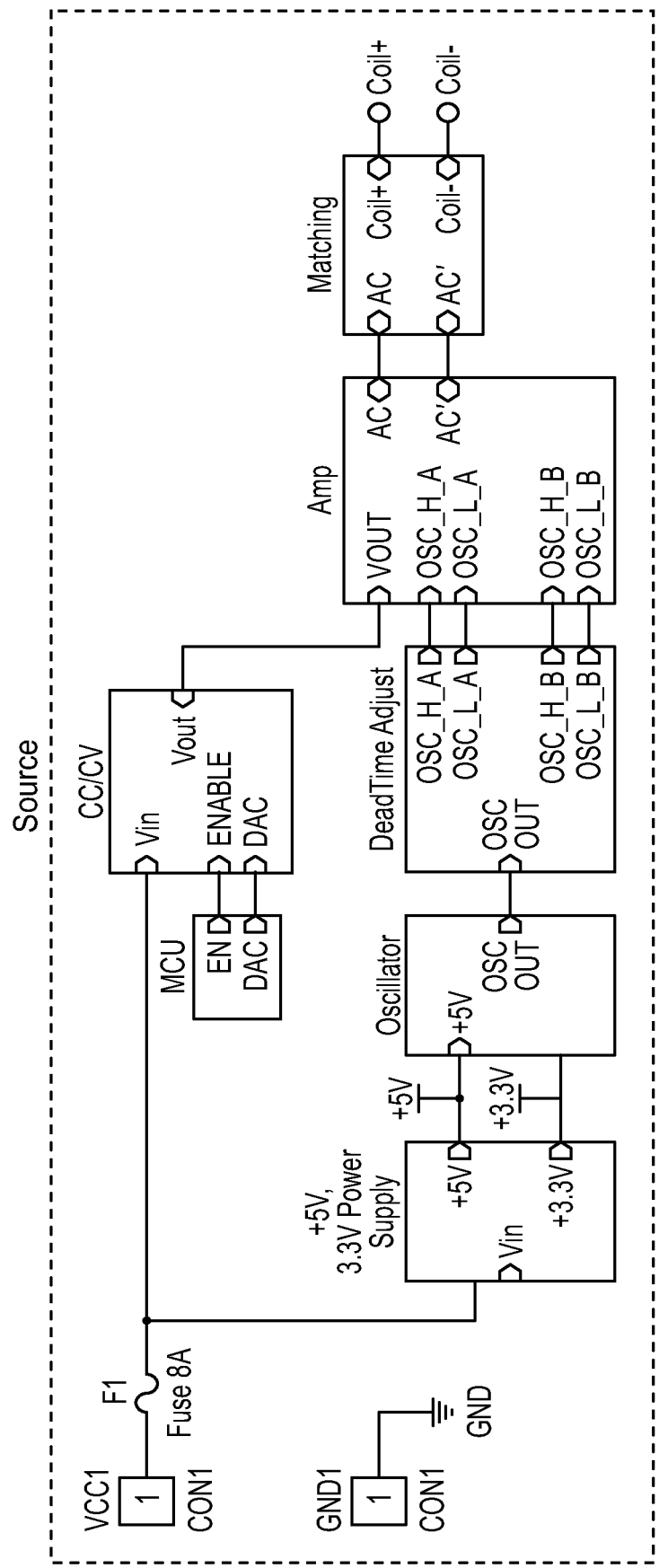
FIG. 12 is a schematic of a system for wireless power transfer in accordance with at least one example of the invention.

Referring now to FIGS. 8A-8C, in some examples, a system 800 for wirelessly transmitting power using resonant magnetic field power transfer can be seen. In some examples, the system 800 includes a device 810 including at least one component 850 to be wirelessly powered. In some examples, the system 800 can be used in a procedure within an orifice 16 or using the orifice 16 as an access point. In some examples, the orifice 16 includes a mouth 16 and the procedure can include a dental procedure. For instance, the example shown in FIG. 8A includes a dental device 810, such as, but not limited to, a dental drill 810. In some examples, with the device 810 including the dental drill 810, the component to be powered can include a drill bit 850, or, more specifically, a rotary actuator that is coupled to the drill bit 850 and configured to rotate the drill bit 850. In some examples, it is contemplated that the system 800 can be used to power the device 810 when inserted into the orifice 16. In some examples, the device 810 can include control circuitry (for instance, disposed within a handle 818 of the device 810) which is wirelessly powered and then, in turn, controls the device 810 or the component 850 of the device 810. The device 810, in some examples, is substantially similar to the device 110 described above. In some examples, the device 810 includes an elongate shaft 814 and a capture element 830 including a capture coil 832 associated with the elongate shaft 814. In other examples, however, the capture element and the capture coil can be associated with a slider of the device 810 (similar to the device 210 described above) or disposed within the handle 818 of the device 810 (similar to the device 310 described above).

In some examples, the system 800 includes a source element 880 for wirelessly supplying power to the device 810. In some examples, the source element 880 includes a source coil 882 and is substantially similar to the source element 480, 780 described above except that the source element 880 is associated with an orifice dilator 860 configured to maintain the orifice 16 sufficiently open and/or spread in order to facilitate insertion of the device 810 and/or other devices or objects used in a procedure. In some examples, the source element 880 includes various layers similar to those described above with respect to the source element 480, 780. In some examples, the orifice 16 is a surgical access point, the orifice dilator 860 being configured to be placed within the orifice 16 to expand the orifice 16 to facilitate insertion of the elongate shaft 814 of the device 810 into the orifice 16. In some examples, insertion of the elongate shaft 814 into the orifice 16 places the capture coil 832 proximate the source coil 882 to allow power to be wirelessly transmitted from the source coil 882 to the capture coil 832. In some examples, the orifice dilator 860 provides a consistent entry path for the device 810 as well as to provide power to the device 810.

In some examples, the source coil 882 receives power 882A, for instance, from being plugged into an electrical outlet or otherwise supplied with power. With the shaft 814 of the device 810 disposed within or otherwise proximate the source coil 882, in some examples, the power 882A can be wirelessly transferred from the source coil 882 to the capture coil 832 to supply power 832A to the device 810. In some examples, the capture coil 832 is electrically coupled directly to the component 850, such that the power 832A is supplied directly to the component 850. In other examples, the capture coil 832 is electrically coupled to control circuitry, such that the power 832A is supplied to the control circuitry to power and control the component 850.

Although examples of the orifice dilator 860 were described herein for use with the mouth 16, in other examples, a similar orifice dilator configured to provide a source element for wireless power transfer can be used for other orifices, including but not limited to the nose, the anus, the vagina, the urethra, the ear, or the like. In some examples, an orifice dilator for an orifice other than the mouth may need to be differently shaped and/or sized than is described herein. In various examples, the orifice dilator can include a different configuration based on the orifice in question with the source coil and shielding residing annularly around the dilated orifice in an anatomically compliant fashion. For an orifice that does not require spreading and/or opening, an annular attachment can be used outside the orifice but encapsulating the access point. Such differently configured shapes and/or sizes are contemplated herein, as the shape and/or size of the orifice dilator 860 for use with the mouth 16 described herein is not intended to be limiting. Additionally, although examples of the orifice dilator 860 were described herein for use with a dental device 810 for use with a dental procedure in the mouth 16, in other examples, a similar orifice dilator can be used to selectively wirelessly power other devices for use in procedures other that dental procedures, such as, but not limited to tonsillectomies, adenoidectomies, procedures done within the airway, and/or procedures done within the digestive system.

Although the example devices 110, 210, 310, 410, 510, 610, 710, 810 were described above as having various components to be powered, this is not intended to be limiting. As such, in various examples, devices (including the devices 110, 210, 310, 410, 510, 610, 710, 810) can include various other components. In some examples, one or more of the devices (including the devices 110, 210, 310, 410, 510, 610, 710, 810) can include an illumination component. In some examples, the illumination component can be configured to illuminate an area by producing at least one of visible light, infrared spectrum light, and ultraviolet spectrum light and/or measure at least one of temperature, distance, and location by producing a visible laser, an infrared spectrum laser, and an ultraviolet spectrum laser. In some examples, one or more of the devices (including the devices 110, 210, 310, 410, 510, 610, 710, 810) can include a component that includes at least one of a data recorder and a data transmitter. In some examples, the data to be recorded and/or transmitted includes one or more of video data, image data, temperature data, stress data, strain data, pressure data, flow rate data, torque data, motion and acceleration data, machine vision data, and motion capture data. In some examples, one or more of the devices (including the devices 110, 210, 310, 410, 510, 610, 710, 810) can include at least one of a cutting and cauterizing component using direct electrical energy; a cutting and cauterizing component using ultrasonic vibrations; a component to activate a rotational motor to rotate a working member; a component to articulate a working member; a component to power actuation of a cutting member; a component to deploy at least one of a staple, a clamp, and an implanted fixation member; and a component to activate a pump.

Referring to FIGS. 9-12, various example system architecture configurations are shown for a source of a system, such as the systems 100, 100', 200, 200', 300, 300', 400, 500, 600, 700, 800 described above, for instance. It is noted that the present subject matter is not intended to be limited to the examples shown in FIGS. 9-12. As such, additional system architecture configurations are contemplated herein and within the scope of the present subject matter.

The examples of FIGS. 9-12 include common components distributed in different ways between a source (such as the source devices described above) and a console external to the source. In some examples, the console is attached to the source using a cord, a wire, a cable, or the like (such as, for instance, the cord 476, 476', 476", 576, 676, 676', 776 described above). The example of FIG. 9 includes amplifier electronics, impedance matching components, and a source coil included with the source and a pre-regulator and all other support electronics included with the console. The example of FIG. 10 includes impedance matching components and a source coil included with the source and all other electronics included with the console. The example of FIG. 11 includes a source coil included with the source and all other electronics included with the console. The example of FIG. 12 includes all electronics except an AC/DC converter included with the source. The example configurations of FIGS. 9 and 12 can be advantageous in that any bends in the cord, wire, or cable leading from the console to the source will not affect impedance matching on the source coil and, therefore, will not significantly alter power delivery. The example configurations of FIGS. 10 and 11 can be advantageous in examples in which the source is configured to work as a repeater. In such examples, the source can be entirely contained externally and positioned within range of a repeater but out of the way of the work space, thereby reducing the amount of cables within a surgical area.

Referring still to FIGS. 9-12, components of each of the example system architecture configurations are now described.

An AC/DC regulator device converts AC energy received, for instance, from a wall outlet, into a DC voltage suitable for the circuitry of the example configurations. In some examples, an output voltage range includes 5-48 V (DC).

A power supply block includes at least one DC/DC regulator to convert the DC voltage from the power supply into a voltage suitable to run the various components (as needed) in all of the other blocks. In various examples, the one or more regulators can include any of various topologies.

An oscillator block is the part of a system for generating a resonant target frequency for which an amplifier runs and impedance matching is tuned. In some examples, this signal controls a frequency for which the amplifier is creating a signal. In some examples, the oscillator block can be incorporated into a microcontroller unit (MCU) block.

A dead-time adjust block includes two functions. First, the dead-time adjust block creates a second signal that is inverted from the main signal received from the oscillator block. Second, the dead-time adjust block adds a gap by adjusting an RC time constant on the signal. The gap, in some examples, can allow for field effect transistors (FETs) within the amplifier to open so that there is not a point in which both FETs are closed at the same time essentially shorting the input through them. Such a condition is often referred to as "shoot through." In some examples, the dead-time adjust block is optional in that some FET drivers invert the signals internally as well as adjust the dead-time automatically.

The MCU block represents the brains of the device. The MCU block, in various examples, can include radiofrequency (RF) telemetry, a graphical user interface (GUI) using, for instance LED, LCD, or the like, as well as various other interfacing controls between the system and any other device. In some examples, the MCU block monitors the system and ensures the system is operating within expected parameters.

A constant current/constant voltage (CC/CV) block is a DC/DC regulator that controls the power into the amplifier. The CC/CV block, in some examples, limits the voltage if the current is below the regulators set limit or controls the current by reducing the voltage to limit the overall power into the amplifier. In some examples, the output of the CC/CV block is tied to the input of the amplifier and is a DC signal.

The amplifier block takes the DC signal and inverts the signal into an AC signal that is passed into the coil source at a specific frequency. The frequency to which the amplifier runs is set by the oscillator.

A matching network block is used to tune the source coil to a specific resonant frequency based on the inductance of the source coil.

In some examples, energy that is received by the capture coil needs to be rectified from an AC signal into a DC signal to run the device. Some devices that rely on AC energy may be able to run natively; however, such devices must be compatible with the frequency of the AC signal and amplitude being received. Oftentimes, to adjust the AC signal, the AC signal is converted to DC energy first. DC energy can also benefit from additional energy storage to act as backup in case the surgical instrument needs more energy than the wireless field can provide or the surgical instrument is moved outside of the field.

In some examples, each of the source coil and the capture coil must be connected to an impedance matching network. The purpose of this network is to make the capture device impedance match the impedance of the source coil, as per the maximum power transfer theorem.

In some examples, the voltage off of the rectifier needs to be regulated off of the rectifier to be used to charge an energy storage device, run the instrument, and/or provide power to any other functions within the surgical instrument.

In some examples, source electronics are needed to take the AC energy from the wall outlet and convert it into a DC energy. The DC energy is then turned into a higher frequency AC signal (for instance, 10 kHz to 100 MHz) that matches the resonant frequency of the source coil.

In some examples, the source can include object detection in order to determine whether a powered device or a non-powered device is being placed through the source. Such a configuration allows the source to be active only when there is a detected powered device inside of the source. In some examples, the sensed object can be specific and the power regulated to match the needs of the device in use.

In some examples, the source can give visual feedback (for instance, via LEDs or other indicators) to indicate when the source is receiving power, when there is a powered device inside the source being activated, as well as multiple other types of necessary or desired information based on a state of the device, the source, and/or the capture.

In some examples, sensor data, video data, and other information communicated from an inserted device can be communicated or transmitted from the device to the source or the console.

The present inventors have recognized various advantages of the subject matter described herein. For instance, in some examples, the examples of systems described herein can be used to power a device, such as, for instance, a surgical device, without the need to tether the device using a power cord or attach a battery to the device. In various examples, the system can reduce the number of trip hazards in the surgical area or other area of use by reducing the number of cords present. The present inventors have recognized the present subject matter can be used to create a balanced, ergonomic device by eliminating uneven weight distribution due to a battery and/or pull from the weight of a cord. While various advantages of the example systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A system for wirelessly transmitting power using resonant magnetic field power transfer, the system comprising:
   a device including at least one component to be wirelessly powered, the device including an elongate shaft and a capture element including a capture coil, wherein the capture coil is disposed within a slider that translates along the elongate shaft of the device, the slider being disposed around the elongate shaft, such that the elongate shaft is disposed through the slider and the capture coil; and
   a source element for wirelessly supplying power to the device, the source element including a source coil disposed around an opening, the opening being sized to allow the slider to fit therein, the source coil being located proximate a surgical access point, wherein, with insertion of the elongate shaft and the slider within the opening of the source for surgical access, the elongate shaft is maneuverable within the opening with the capture coil within the slider being disposed sufficiently proximate the source coil to allow power to be wirelessly transmitted from the source coil to the capture coil to power the at least one component of the device.

2. The system of claim 1, wherein the capture coil includes a conductive material having a resistivity lower than $12\times10^{-8}$ ohm-meters, the capture element including:
   a first capture layer including a material having a skin depth that is less than a thickness of the first capture layer;
   a second capture layer including a material having a relative permeability greater than 80 at a resonant frequency; and
   a third capture layer including a non-conductive material, wherein the capture coil is disposed between the second capture layer and third capture layer.

3. The system of claim 1, wherein the source coil includes a conductive material having a resistivity lower than $12\times10^{-8}$ ohm-meters, the source element including:
   a first source layer including a material having a skin depth that is less than a thickness of the first source layer;
   a second source layer including a material having a relative permeability greater than 80 at a resonant frequency; and
   a third source layer including a non-conductive material, wherein the source coil is disposed between the second source layer and third source layer.

4. The system of claim 1, wherein the source coil includes a solenoid coil.

5. The system of claim 1, wherein the source coil includes a planar coil.

6. The system of claim 1, wherein the at least one component of the device includes an illumination component, wherein the illumination component is configured to at least one of:
   illuminate an area by producing at least one of visible light, infrared spectrum light, and ultraviolet spectrum light; and
   measure at least one of temperature, distance, and location by producing a visible laser, an infrared spectrum laser, and an ultraviolet spectrum laser.

7. The system of claim 1, wherein the at least one component of the device includes at least one of a data recorder and a data transmitter, wherein the data includes at least one of:
   video data;
   image data;
   temperature data;
   stress data;
   strain data;
   pressure data;
   flow rate data;
   torque data;
   motion and acceleration data;
   machine vision data; and
   motion capture data.

8. The system of claim 1, wherein the at least one component of the device includes at least one of:
   a cutting and cauterizing component using direct electrical energy;
   a cutting and cauterizing component using ultrasonic vibrations;
   a component to activate a rotational motor to rotate a working member;
   a component to articulate a working member;
   a component to power actuation of a cutting member;
   a component to deploy at least one of a staple, a clamp, and an implanted fixation member; and
   a component to activate a pump.

9. The system of claim 1, wherein the source element is associated with an attachment member configured to attach directly to a patient, the attachment member including the source coil disposed within the attachment member, wherein the surgical access point is an incision, the attachment member being configured to be placed at the incision so that insertion of the elongate shaft into the incision places the capture coil proximate the source coil to allow power to be wirelessly transmitted from the source coil to the capture coil.

10. The system of claim 1, wherein the source element is associated with an orifice dilator including the source coil disposed within the orifice dilator, wherein the surgical access point is an orifice, the orifice dilator being configured to be placed within the orifice to expand the orifice to facilitate insertion of the elongate shaft of the device into the orifice, wherein insertion of the elongate shaft into the orifice places the capture coil proximate the source coil to allow power to be wirelessly transmitted from the source coil to the capture coil.

11. The system of claim 1, wherein the source element is associated with an access device including the source coil associated with the access device, the access device being disposed within the patient to form the surgical access point, wherein insertion of the elongate shaft into the access device places the capture coil proximate the source coil to allow power to be wirelessly transmitted from the source coil to the capture coil.

12. The system of claim 11, wherein the source coil is disposed within an attachment removably engageable with the access device.

13. The system of claim 11, wherein the source coil is disposed within the access device.

14. A system for wirelessly transmitting power using resonant magnetic field power transfer, the system comprising:
   a device including at least one component to be wirelessly powered, the device including an elongate shaft and a capture element including:
      a capture coil disposed within a slider that translates along the elongate shaft of the device, the slider being disposed around the elongate shaft, such that the elongate shaft is disposed through the slider and the capture coil;
      a first capture layer including a material having a skin depth that is less than a thickness of the first capture layer;
      a second capture layer including a material having a relative permeability greater than 80 at a resonant frequency; and
      a third capture layer including a non-conductive material, wherein the capture coil is disposed between the second capture layer and third capture layer; and
   a source element for wirelessly supplying power to the device, the source element including:
      a source coil;
      a first source layer including a material having a skin depth that is less than a thickness of the first source layer;
      a second source layer including a material having a relative permeability greater than 80 at a resonant frequency; and
      a third source layer including a non-conductive material, wherein the source coil is disposed between the second source layer and third source layer, wherein the source coil is disposed around an opening, the opening being sized to allow the elongate shaft of the device to fit therein, the source being located proximate a surgical access point, wherein, with insertion of the slider within the opening of the source for surgical access, the capture coil is disposed sufficiently proximate the source coil to allow power to be wirelessly transmitted from the source coil to the capture coil to power the at least one component of the device.

15. The system of claim 14, wherein the source element is associated with an attachment member configured to attach directly to a patient, the attachment member including the source coil disposed within the attachment member, wherein the surgical access point is an incision, the attachment member being configured to be placed at the incision so that insertion of the elongate shaft into the incision places the capture coil proximate the source coil to allow power to be wirelessly transmitted from the source coil to the capture coil.

16. The system of claim 14, wherein the source element is associated with an orifice dilator including the source coil disposed within the orifice dilator, wherein the surgical access point is an orifice, the orifice dilator being configured to be placed within the orifice to expand the orifice to facilitate insertion of the elongate shaft of the device into the orifice, wherein insertion of the elongate shaft into the orifice places the capture coil proximate the source coil to allow power to be wirelessly transmitted from the source coil to the capture coil.

17. The system of claim 14, wherein the source element is associated with an access device including the source coil associated with the access device, the access device being disposed within the patient to form the surgical access point, wherein insertion of the elongate shaft into the access device places the capture coil proximate the source coil to allow power to be wirelessly transmitted from the source coil to the capture coil.

18. A system for wirelessly transmitting power using resonant magnetic field power transfer, the system comprising:
   a device including at least one component to be wirelessly powered, the device including an elongate shaft and a capture element including a capture coil, wherein the capture coil is disposed within a slider that translates along the elongate shaft of the device, the slider including a slider opening and being disposed around the elongate shaft, such that the elongate shaft is disposed through the slider opening and the capture coil; and
   a source element for wirelessly supplying power to the device, the source element including a source coil disposed around a source element opening, the source element opening being sized to allow the slider including the capture coil to fit therein, the source coil being located proximate a surgical access point, wherein, with insertion of the slider within the source element opening, the elongate shaft is maneuverable within the slider opening and the source element opening for surgical access while maintaining the capture coil within the slider sufficiently proximate the source coil to allow power to be wirelessly transmitted from the source coil to the capture coil to power the at least one component of the device.

19. The system of claim 18, wherein the source element is associated with an attachment member configured to attach directly to a patient, the attachment member including the source coil disposed within the attachment member, wherein the surgical access point is an incision, the attachment member being configured to be placed at the incision so that insertion of the slider into the source element opening places the capture coil proximate the source coil to allow power to be wirelessly transmitted from the source coil to the capture coil.

20. The system of claim 18, wherein the source element is associated with an access device including the source coil associated with the access device, the access device being disposed within the patient to form the surgical access point, wherein insertion of the slider into the source element opening places the capture coil proximate the source coil to allow power to be wirelessly transmitted from the source coil to the capture coil.

* * * * *